US012569301B2

(12) United States Patent (10) Patent No.: US 12,569,301 B2
Clayton et al. (45) Date of Patent: Mar. 10, 2026

(54) SURGICAL NAVIGATION SYSTEM FOR ALIGNMENT OF A SURGICAL INSTRUMENT

(71) Applicant: Alphatec Spine, Inc., Carlsbad, CA (US)

(72) Inventors: John B. Clayton, Superior, CO (US);
Kevin J. Frank, Louisville, CO (US);
Kevin T. Foley, Germantown, TN (US);
David A. Vaughan, Superior, CO (US);
Jeff Justis, Germantown, TN (US)

(73) Assignee: Alphatec Spine, Inc., Carlsbad, CA (US)

( * ) Notice: Subject to any disclaimer, the term of this patent is extended or adjusted under 35 U.S.C. 154(b) by 948 days.

(21) Appl. No.: 17/769,527

(22) PCT Filed: Oct. 16, 2020

(86) PCT No.: PCT/US2020/056013
§ 371 (c)(1),
(2) Date: Apr. 15, 2022

(87) PCT Pub. No.: WO2021/076909
PCT Pub. Date: Apr. 22, 2021

(65) Prior Publication Data
US 2024/0130795 A1 Apr. 25, 2024
US 2024/0225742 A9 Jul. 11, 2024

Related U.S. Application Data

(60) Provisional application No. 62/923,284, filed on Oct. 18, 2019.

(51) Int. Cl.
*A61B 34/20* (2016.01)
*A61B 6/04* (2006.01)
(Continued)

(52) U.S. Cl.
CPC ............ *A61B 34/20* (2016.02); *A61B 6/0421* (2013.01); *A61B 34/10* (2016.02); *A61B 34/30* (2016.02);
(Continued)

(58) Field of Classification Search
CPC ......... A61B 34/10; A61B 34/20; A61B 34/30; A61B 6/0421; A61B 90/39; A61B 2034/107; A61B 2034/2057
See application file for complete search history.

(56) References Cited

U.S. PATENT DOCUMENTS 7,630,753 B2 12/2009 Simon et al.
7,689,014 B2 3/2010 Abovitz et al.
(Continued)

FOREIGN PATENT DOCUMENTS

WO WO-2018167246 A1 * 9/2018 ............. A61B 34/20

OTHER PUBLICATIONS

PCT International Preliminary Report on Patentability issued to counterpart Application No. PCT/US2020/056013 dated Jan. 31, 2022.
(Continued)

*Primary Examiner* — John D Li
(74) *Attorney, Agent, or Firm* — Robert Winn

(57) ABSTRACT
A surgical navigation method utilizing a computer system. The method includes the steps of: (a) fixing a camera relative to a surgical site on a patient such that the camera does not move relative to the surgical site; (b) restraining the body portion of the patient which includes the surgical site relative to an operating table supporting the patient, such that the body portion does not move relative to the operating table; and (c) detecting with the camera the position of a medical instrument having a tracker array.

9 Claims, 24 Drawing Sheets

(51) Int. Cl.

| | | |
|---|---|---|
| *A61B 34/10* | (2016.01) | |
| *A61B 34/30* | (2016.01) | |
| *A61B 90/00* | (2016.01) | |

(52) U.S. Cl.

CPC ........ *A61B 90/39* (2016.02); *A61B 2034/107* (2016.02); *A61B 2034/2057* (2016.02)

(56) References Cited

U.S. PATENT DOCUMENTS

| | | | |
|---|---|---|---|
| 8,738,181 | B2 | 5/2014 | Greer et al. |
| 8,886,286 | B2 | 11/2014 | Graumann et al. |
| 9,757,087 | B2 | 9/2017 | Simon et al. |
| 9,949,798 | B2 | 4/2018 | Weir |
| 10,603,120 | B2 | 3/2020 | Steinle et al. |
| 10,660,712 | B2 | 5/2020 | Kostrzewski et al. |
| 2003/0028091 | A1* | 2/2003 | Simon .................... A61B 34/10 |
| | | | 600/407 |
| 2006/0064005 | A1 | 3/2006 | Triano et al. |
| 2014/0247336 | A1* | 9/2014 | Vilsmeier .............. A61B 34/20 |
| | | | 348/77 |
| 2016/0242934 | A1 | 8/2016 | van der Walt et al. |
| 2018/0049839 | A1 | 2/2018 | Seong et al. |
| 2018/0110573 | A1* | 4/2018 | Kostrzewski .......... A61B 34/10 |
| 2018/0125584 | A1 | 5/2018 | Lang |
| 2018/0318017 | A1 | 11/2018 | Fanson et al. |
| 2019/0117318 | A1 | 4/2019 | Charron et al. |
| 2019/0159848 | A1 | 5/2019 | Quaid et al. |
| 2020/0138518 | A1* | 5/2020 | Lang .................. A61B 17/1666 |

OTHER PUBLICATIONS

PCT Notification of Transmittal of the International Search Report and the Written Opinion of the International Searching Authority, or the Declaration issued to counterpart Application No. PCT/US2020/056013 dated May 11, 2021.

Faldini et al. "Power-assisted pedicle screws placement: Is it as safe and as effective as manual technique? Narrative review of the literature and our technique", Musculoskeletal Surgery, 2021, vol. 105, p. 117-123, Springer.

Lieberman et al. "Robotic-Assisted Pedicle Screw Placement During Spine Surgery", JB&JS Essential Surgical Techniques,2020, 10(2), p. 1-15.

Rawicki et al. "Current state of navigation in spine surgery" Annals of Translational Medicine, 2021, 9(1), p. 85.

Overley et al. "Navigation and Robotics in Spinal Surgery: Where Are We Now?" Congress of Neurological Surgeons, Mar. 2017, vol. 80, No. 3, p. S86-S99.

* cited by examiner

**Instantaneous 8
Sphere Rigid Body**

95

250 — Start

251 — Display Setup Status

252 — Display Instructions for Acquiring Images

253 — Receive Images

254 — Automatically Register Images to Camera

255 — Display Images

256 — Enable Planning and Display Plans

257 — Display Guidance View for Aligning the Robot to Plan

258 — Display Instruments on the Images

259 — Done

280 — Volume

281 — Dilate

282 — Erode

283 — Mask

284 — Connected Component Analysis

285 — Compute Geometric Features

286 — Remove Outliers Using Geometric Features

287 — Compute IPD Error

288 — Remove Outliers Using IPD Error

289 — Remove Outliers Using RANSAC

290 — Done

SURGICAL NAVIGATION SYSTEM FOR ALIGNMENT OF A SURGICAL INSTRUMENT

I. BACKGROUND OF INVENTION

In the field of image-guided surgery or surgical navigation, a camera (often called a "localizing camera") in the operating room tracks the positions of surgical tools in three-dimensional space. This positional information is transmitted from the localizing camera to a computer. The computer's monitor displays multi-planar, three-dimensional radiographic images of the patient's anatomy relevant to the surgical procedure and which have been uploaded into the computer. The patient's anatomy as positioned in the operating room is registered to the radiographic image data using a probe or registration array that is tracked by the localizing camera. In image-guided surgery, registration is the process that transforms the three-dimensional radiographic data set (image space) so that it correlates with the three-dimensional coordinates of the corresponding patient anatomy (surgical space). Following registration of the relevant anatomical structure, a navigation system 100 such as seen in FIG. 1 can present the positions of the tracked surgical tools relative to the displayed radiographic anatomy on display 102. The tracked surgical tools or instruments will have their own tracking array 103 with IR marker elements, allowing the system to detect and track the surgical instruments through localizing camera 101. In order for this process to be accurate, the three-dimensional spatial relationship between the localizing camera and the patient's anatomical structure must be known and maintained. If the localizing camera moves or if the patient's anatomical structure moves during surgery, the navigation system's accuracy deteriorates. In order to compensate for this issue, a tracked tool known as a dynamic reference frame 104 is fixed in relationship to the patient's anatomical structure. If the patient's anatomy and the localizing camera move relative to one another, their three-dimensional relationship is recalculated by the navigation system computer and the registration solution is updated. Typically, the dynamic reference frame is fixed to a clamp that is in turn fixed to the patient's anatomy near the surgical site 105.

While the above measures can serve to maintain the accuracy of image-guided surgery, they have limitations. In order to track the dynamic reference frame, the localizing camera measures the spatial coordinates of markers on the reference frame 104 in the x-axis, y-axis, and z-axis. The accuracy of these measurements changes as the viewing angle changes between the camera and the markers. It is a common practice to move the camera to maintain its line of sight for localizing the dynamic reference frame to accommodate such things as microscopes, various instruments, and additional operating room personnel entering the surgical field. As well, the patient is often repositioned during surgery, such as occurs when rotating the operating room table and raising or lowering the table. In these instances, navigational error is inadvertently induced when the camera moves relative to the markers on the dynamic reference frame.

There remains a need for instruments and techniques that minimize or eliminate relative motion between the localizing camera and the dynamic reference frame during image-guided surgery.

II. SUMMARY OF SELECTED EMBODIMENTS OF INVENTION

One embodiment of the invention is a surgical navigation method utilizing a computer system. The method includes:

(a) fixing a camera relative to a surgical site on a patient such that the camera does not move relative to the surgical site; (b) restraining the body portion of the patient which includes the surgical site relative to an operating table supporting the patient, such that the body portion does not move relative to the operating table; and (c) detecting with the camera the position of a medical instrument having a tracker array.

Another embodiment includes positioning a registration array over the surgical site and generating a 3D radiological image which is registered to the camera using the registration array. The registration array is removed from the patient, after which the camera tracks the position of the surgical instrument during a surgical procedure.

A further embodiment of the invention is an OR table which includes at least two, opposing, inwardly, and downwardly sloping pelvis support pads. The pelvis support pads have at least three layers of foam material having different densities, with a patient interface layer being the least dense of the at least three layers and the bottom layer being the most dense the layers. Fixation sheets will be used to immobilize the patient relative to the pelvis support pads.

Additional embodiments are described in the following drawings and detailed description.

III. BRIEF DESCRIPTION OF THE DRAWINGS

IV. DETAILED DESCRIPTION OF SELECTED EMBODIMENTS

Figure 1:
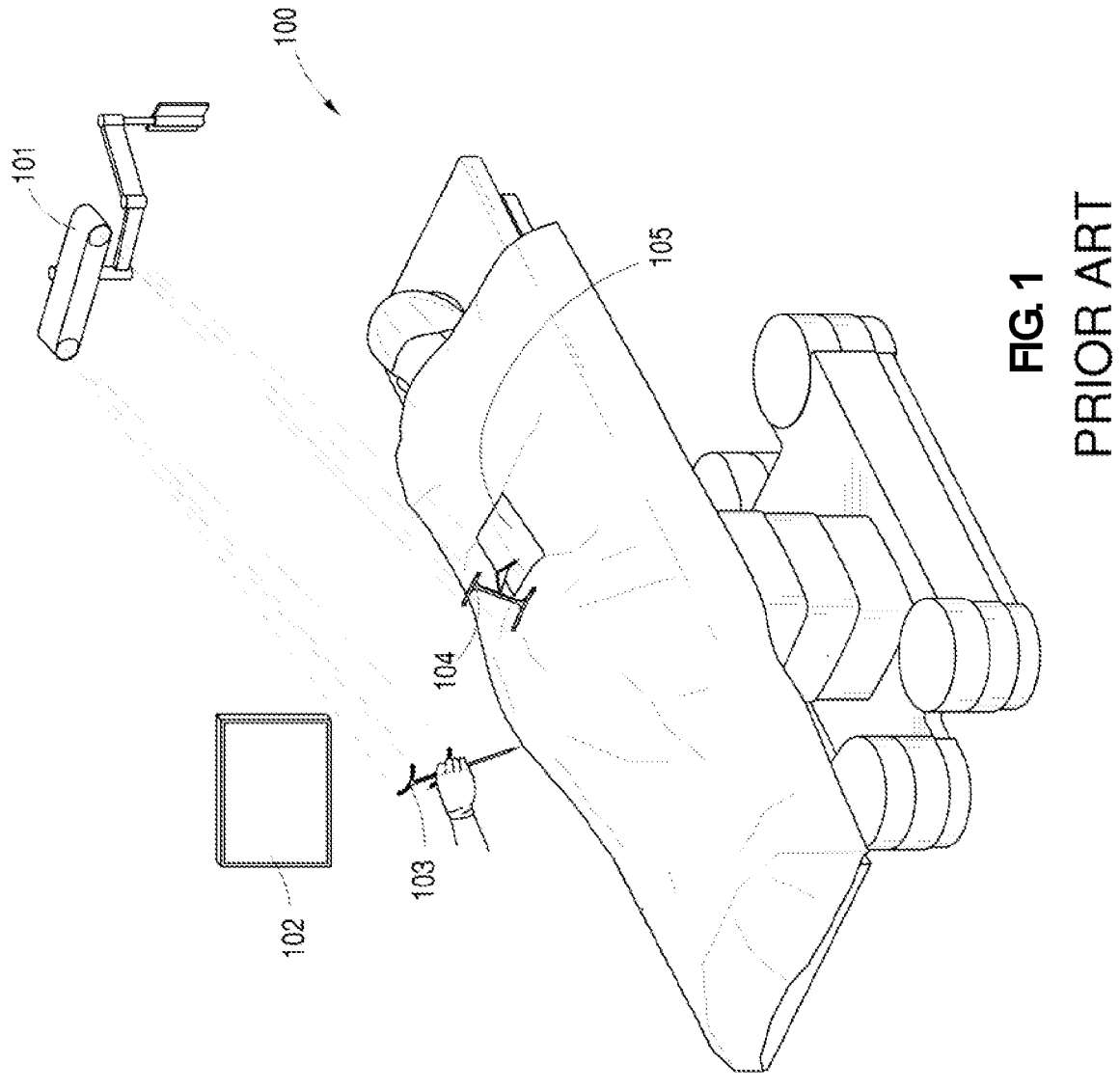
FIG. 1 illustrates a prior art surgical navigation system.
Figure 2A:
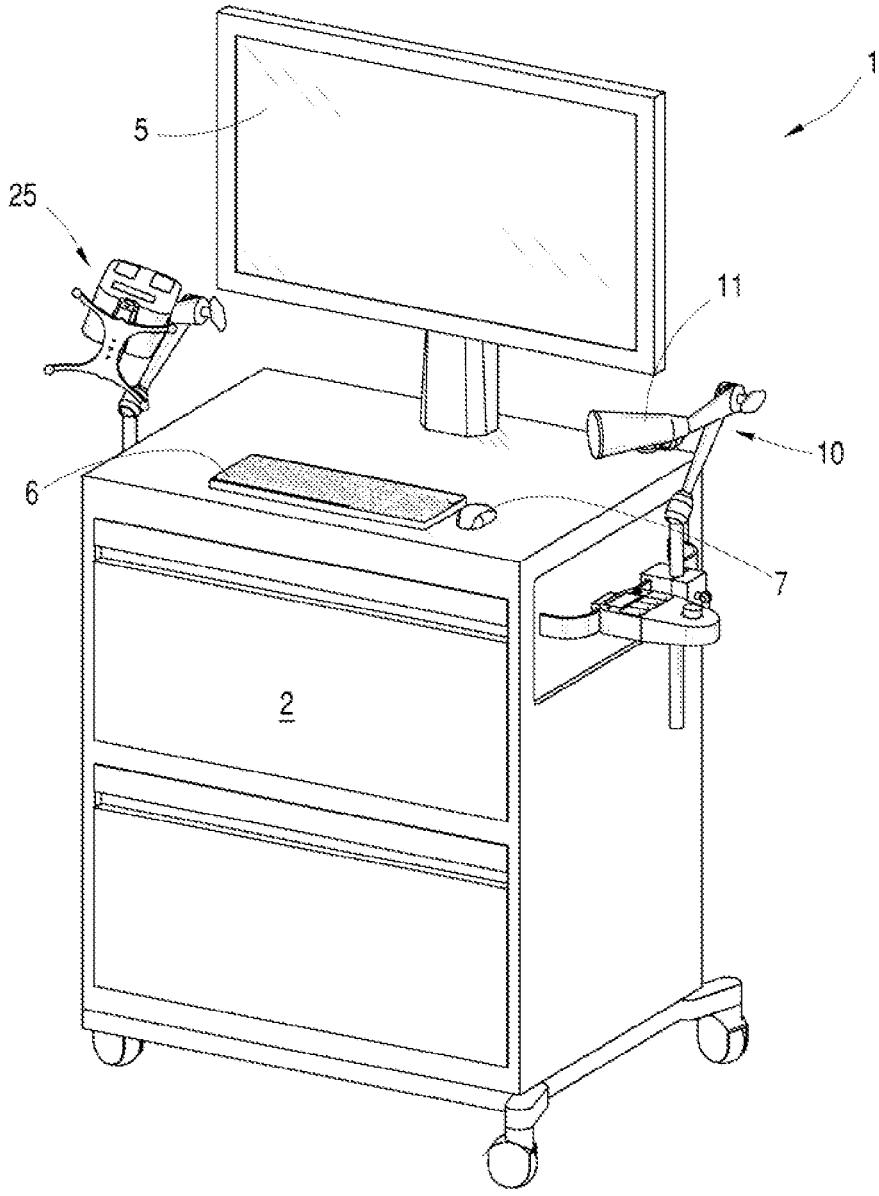
FIG. 2A illustrates a work station encompassing the hardware of the surgical navigation system of the present invention.

One example of the components utilized in the navigation system 1 of the present invention is suggested in FIG. 2A. These components include a system station or movable cart 2. Mounted on station 2 is a display 5 and user interface components such as conventional keyboard 6 and mouse 7. FIG. 2 also shows detachably mounted on the station 2 the optical sensor 10 (e.g., camera 11) and the trajectory system 25, both of which will be described in greater detail below.

Figure 2B:
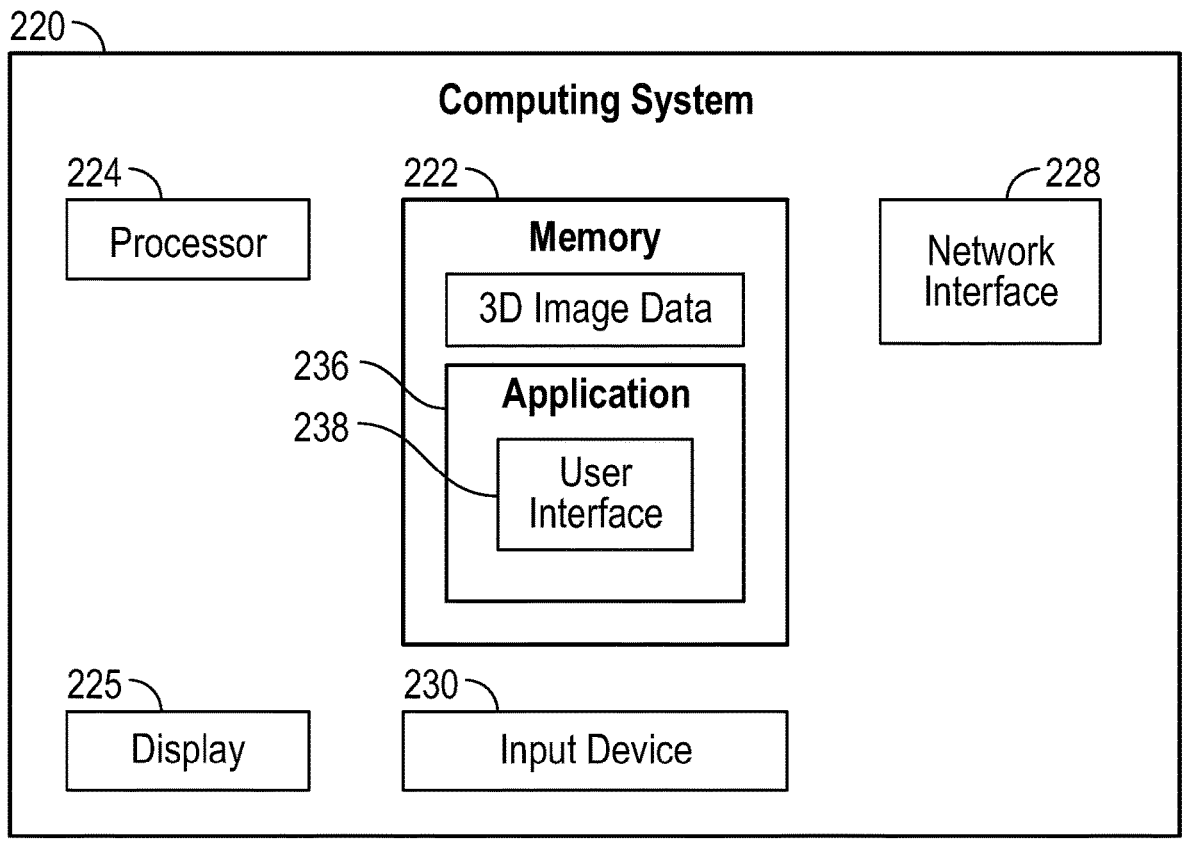
FIG. 2B illustrates a diagram of a computer system running software required to operate the surgical navigation system.

The navigation system will include a computer system 220 which is illustrated as a system diagram in FIG. 2B. The computer system 220 may include memory 222, processor 224, display 5 referenced above, network interface 228, and input device 230. Memory 222 may store application 236 and/or CT data 234. Application 236 may, when executed by processor 224, cause display 5 to present user interface 238. Processor 224 may be a general purpose processor, a specialized graphics processing unit (GPU) configured to perform specific graphics processing tasks while freeing up the general purpose processor to perform other tasks, and/or any number or combination of such processors. Keyboard 6 and mouse 7 serve as data input devices. Alternatively, display 5 may be touch sensitive and/or voice activated, enabling display 5 to serve as both an input and output device. Network interface 228 may be configured to connect to a network whether wired or wireless. Through network interface 228, computing system 220 will receive data from and send commands to related devices such as camera 11 and trajectory system 25. Computing system 220 may also receive image data, e.g., computed tomographic (CT) image data, of a patient from a server, for example, a hospital server, internet server, or other similar servers, for use during surgical planning and execution. Application 236 may be one or more software programs stored in memory 222 and executed by processor 224. These software programs will carry out the computer related functions described below, including generating the navigation images and various user interfaces.

Figure 3A:
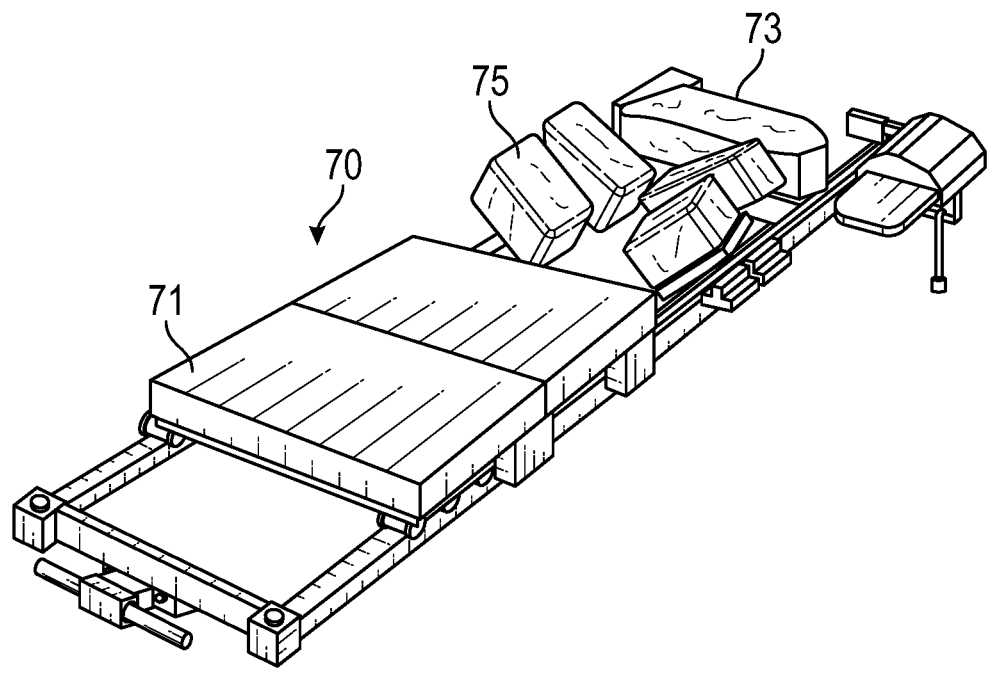
FIG. 3A illustrates the patient support frame of an OR table according to the present invention.
Figure 3B:
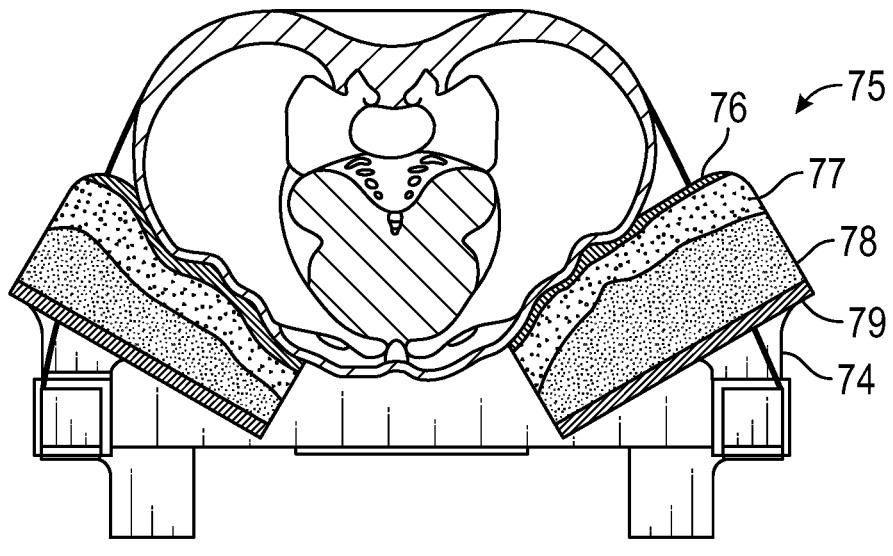
FIG. 3B illustrates a cross-sectional view of a patients hips resting on pelvis support pads of the OR table.

Although many aspects of the present invention relate to software manipulation of medical images, one embodiment of the invention relates to an improvement in OR tables. For reasons which will be apparent below, one important feature to certain embodiments of the invention is securing the patient's anatomy undergoing surgery against movement relative to the OR table. FIGS. 3A and 3B suggest an OR table with modifications which create a stabilizing surface to help secure the patient against movement during the surgical procedure. FIG. 3A illustrates the top portion of a rail-type OR table 70 (e.g., an Allen Advanced or Jackson radiolucent OR table) having a series of patient support surfaces or pads such as legs support pad 71, pelvis support pads 75, and head support pad 73. The support pads may also sometimes be referred to as "table adapters." FIG. 3B shows a cross-section of a patient's pelvis or hip structure in the prone orientation being positioned on the pelvis support pads 75 and likewise shows the structure of the pelvis support pads 75. This embodiment of pelvis support pad 75 includes at least three layers of a foam material, with each layer having a different density or rigidity, with the top layer (or "patient interface layer") 76 being the least rigid of the layers and the bottom layer 78 being the most rigid of the layers. The bottom layer 78 is fixed (e.g., by an adheasive) to the very rigid backing layer 79, which in turn is attached to the support bracket 74 connected to a rail of the OR table.

In one example embodiment, top layer 76 has a rigidity or hardness on the Shore A scale of between 30 and 40, middle layer 77 has a hardness of between 50 and 70, bottom layer 78 a hardness of between 70 and 90, and backing layer 79 having a still greater hardness. Typically, the layer thicknesses will vary anywhere between 0.5 centimeters to 10 centimeters, and more preferably, 1 to 5 centimeters. In certain embodiments, the layers will increase in thickness from top layer 76 to bottom layer 78. In a preferred embodiment, the layers are formed of a visco elastic poly-urethane foam material.

Figure 4:
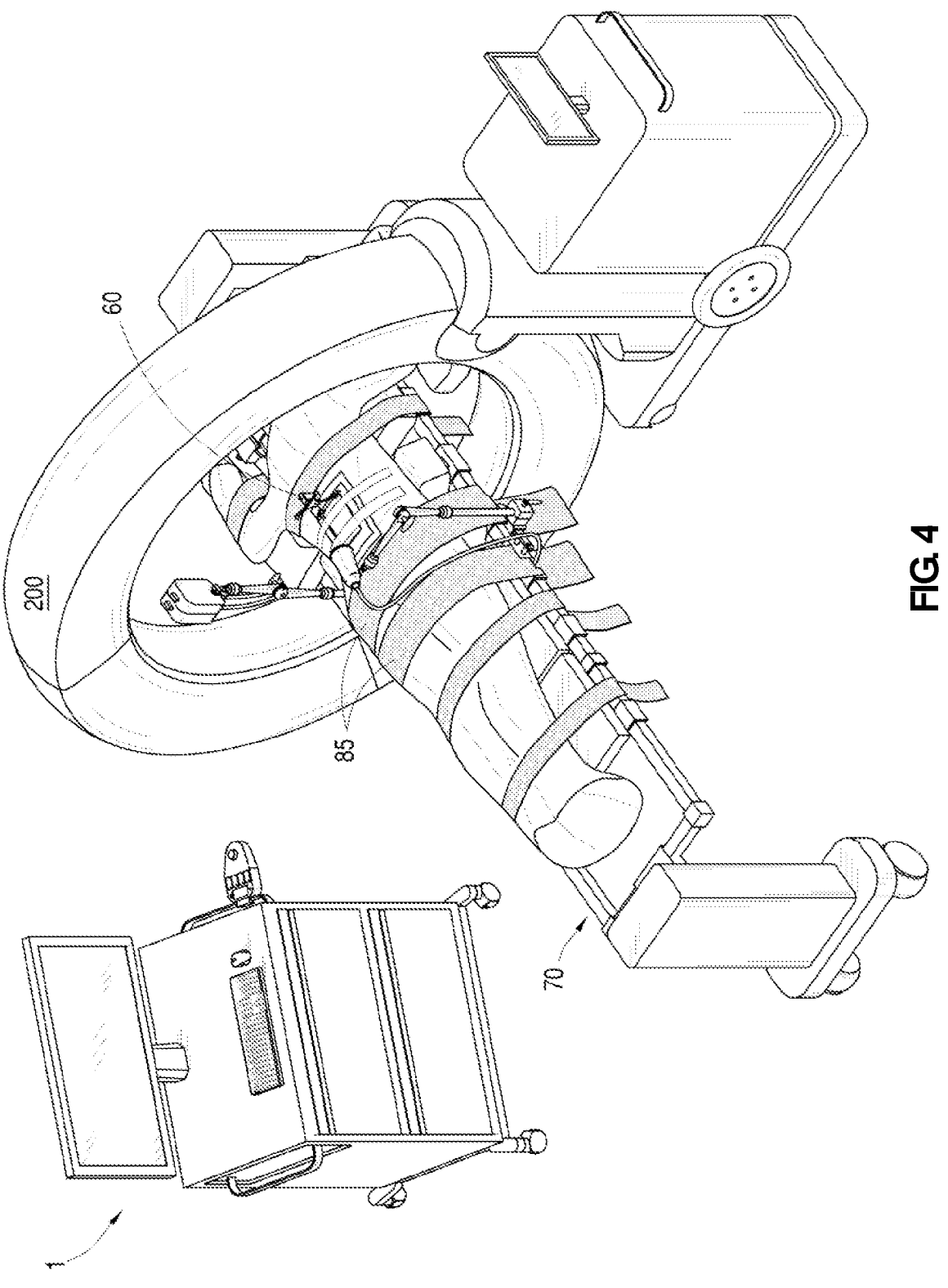
FIG. 4 illustrates the surgical navigation system employed while a radiological image is being created of the surgical site.

FIGS. 4 and 5 illustrate a patient in a prone position on the OR table 70. It will be understood that in this position, the two, opposing, inwardly, and downwardly sloping pelvis support pads 75 act to cradle the patient's pelvis or hip anatomy and allows the patient's weight to help stabilize his or her position. FIG. 4 also suggests how a series of patient fixation sheets 85 will be stretched over the patient and secured to the OR table on each side of the patient in order to further immobilize the patient's pelvis and thoracic spine region. Typically, the fixation sheets are breathable elastic fabric sheets or bands between 4" and 18" in width in order to distribute the force applied to the patient's body and not restrict circulation. In one example, the fixation sheets may be iFIX Fleece strips available from Interventional Systems USA of Stamford, CT. However, the fixation sheets could alternatively be coflex elastic bandages, custom designed belts with adequate padding, or virtually any means to securely fix the relevant patient anatomy safely to the OR table while not impeding the surgical process.

Figure 5A:
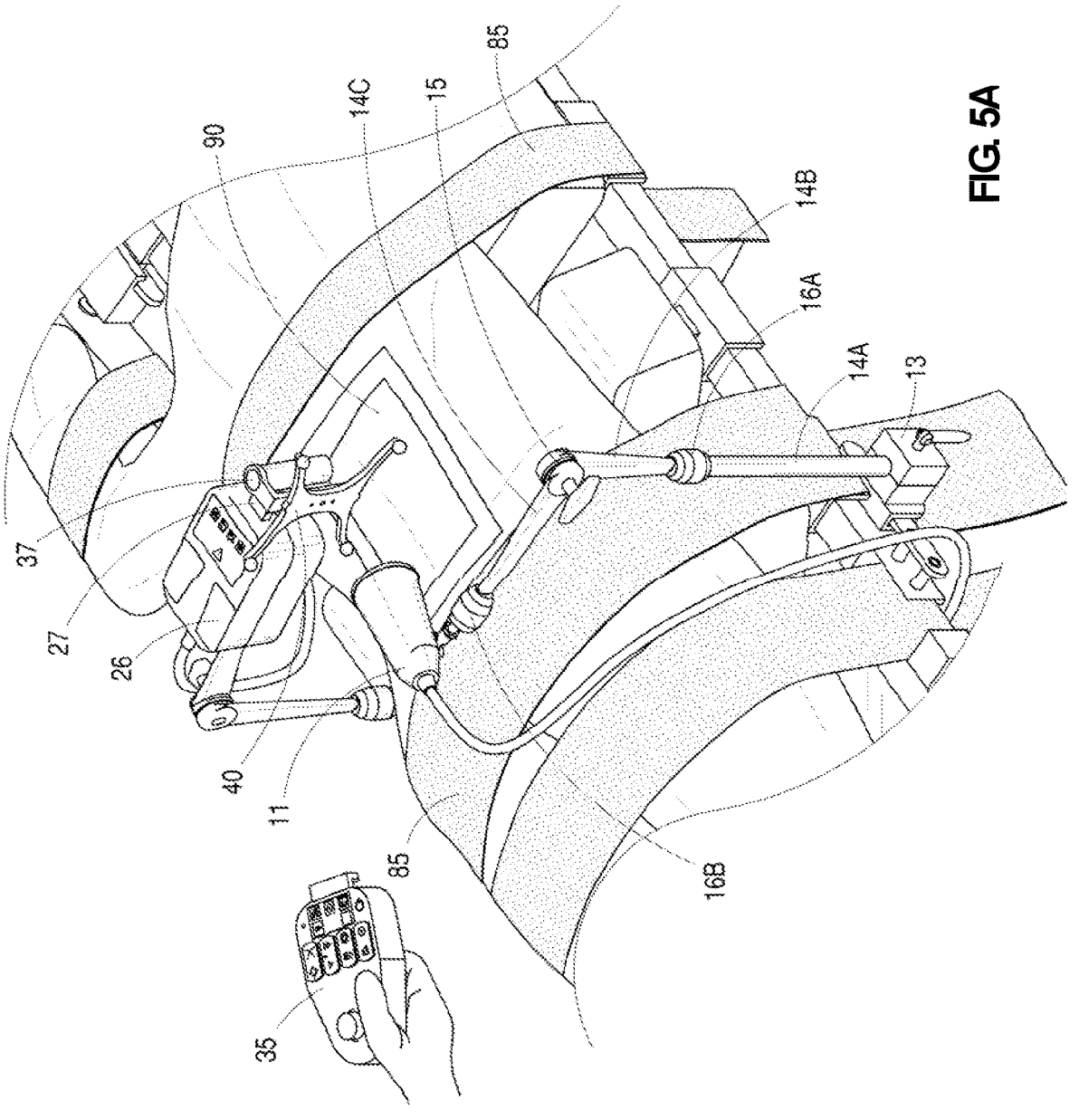
FIG. 5A illustrates the instrument guide being positioned over the surgical site.
Figure 5B:
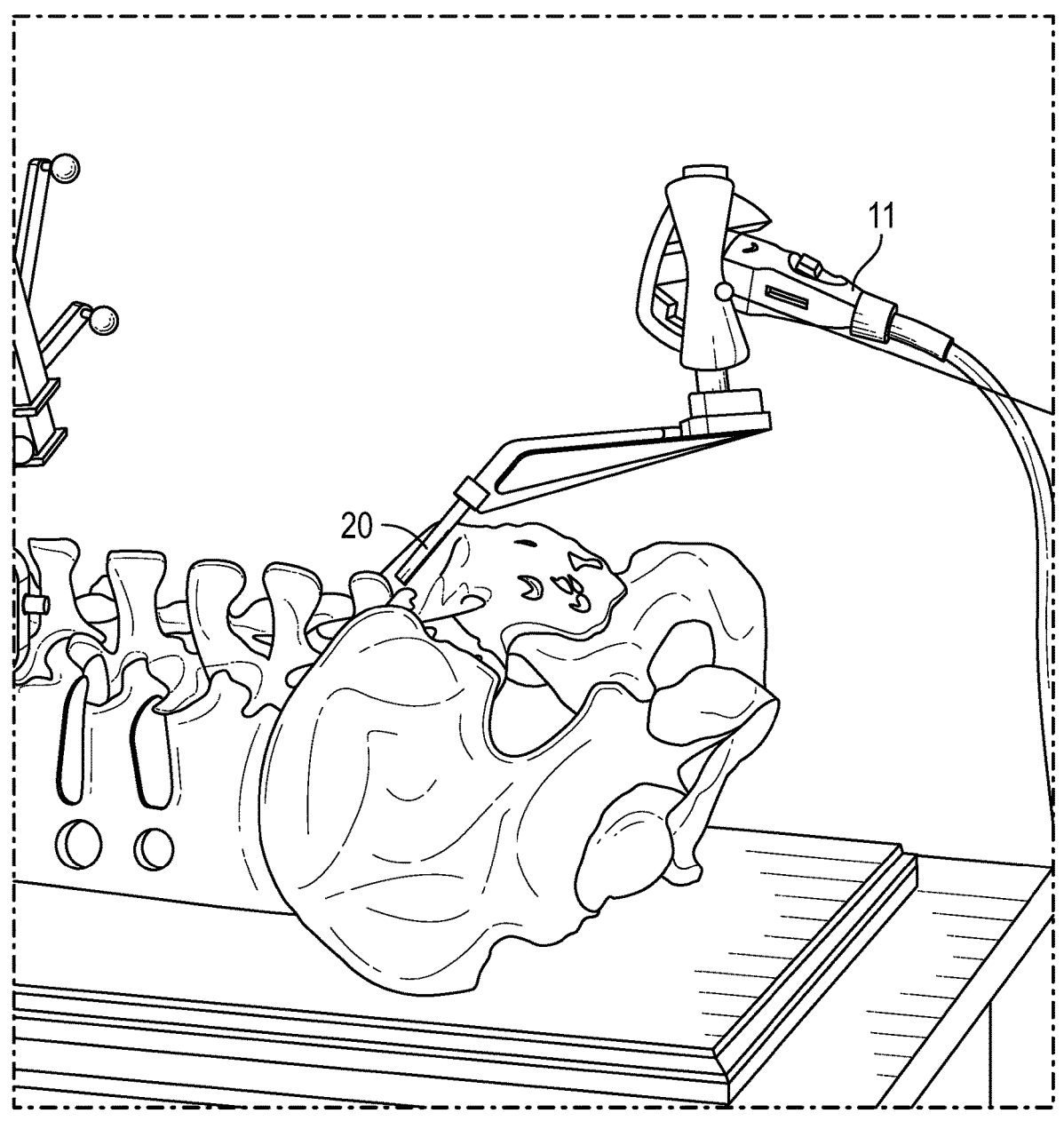
FIG. 5B illustrates a method of mounting a camera on a patient's skeletal structure.

With the patient secured to the OR table, FIG. 5A allows visualization of one method of the present invention which includes fixing an optical sensor (e.g., camera 11 in FIG. 5A) such that the camera 11 does not move relative to the surgical sight 90. In the FIG. 5A embodiment, this relative fixation is accomplish by immobilizing the patient to the OR table as described above and then fixing camera 11 to the OR table by any convention means. FIG. 5A shows the bed mounting bracket 13 clamping to a rail of the OR table and several positioning arm segments 14A to 14C connecting mounting bracket 13 to camera 11. The locking sleeve 16A may be loosened to allow position arm segment 14B to be rotated with respect to arm segment 14B, and then locking sleeve 16A is tightened in order to lock the relative position of the arm segments. Arm segment 14B may also extend telescopically from arm segment 14A with locking sleeve 16A also fixing this telescopic relationship. Similarly, locking hinge 15 allows the positioning arm segment 14C to rotate with respect to 14B and then be locked into the desired relative position. Locking sleeve 16B allows camera 11 to rotate with respect to arm segment 14C and then be locked into position. Employing this mechanical structure, camera 11 will be position such that it does not interfere with the surgical procedure, but still maintains in its field of view any tracking arrays utilized during the surgical procedure (e.g., the tracking array 40 seen in FIG. 5A, whose function is explained in more detail below). In the illustrated embodiment, camera 11 may be a monocular localization camera available from Intellijoint Surgical, Inc. of Kitchener, Canada.

Although FIG. 5A shows relative fixation between the surgical site and camera by fixing the patient and camera to the OR table, this relative fixation could be secured by other methods. For instance, if the OR table is securely fixed to the operating room floor, then the camera could likewise be fixed to the OR floor. With the patient immobilized with respect to the OR table, the camera and surgical site are relatively fixed to one another. In a still further embodiment suggested in FIG. 5B, the camera 11 could be fixed to the skeletal anatomy of the patient, one example of which could be the camera 11 mounted to a rod 20 or similar structure which is in turn pinned to the hip or other pelvic bones of the patient or clamped directly to the spine of the patient. In this latter method, immobilization of the patient relative to the OR table may be less important for a surgical site (e.g., lumbar spine) which is comparatively immobile relative to the pelvis. In preferred embodiments, camera 11 is equipped with an accelerometer and/or gravimeter. These sensors may act to detect any unintentional movement of camera 11 (e.g., surgical personnel inadvertently bumping the camera). If these sensors detect camera movement, the system may generate a warning of camera movement which could possibly have changed the relative fixation between the camera and surgical site.

As suggested above, the patient's anatomy as positioned in the operating room is registered to the radiographic image data using a probe or registration array that may be tracked by the camera. FIG. 4 shows an intraoperative X-ray imaging system 200 (e.g., the O-arm Imaging System available from Medtronic, Inc. of Minneapolis, MN) positioned to create a radiographic image of the patient's anatomy at the surgical site. Positioned over the surgical site is the registration array 60. A more detailed description of registration array 60 is provided further below. For present, it is sufficient to note that with camera 11 fixed relative to the patient's anatomy and detecting the registration array 60, the registration process can transform the three-dimensional radiographic data set so that it correlates with the three-dimensional coordinates of the corresponding patient anatomy as positioned on the OR table.

Typically, surgical navigation systems employ some type of surgical instrument alignment guide. The alignment guide is often a cylindrical tube or sleeve through which surgical instruments such as awls, driver/screw assemblies, etc. are directed. Viewing FIG. 5A, another aspect of the invention is a system and method (and the related software) for orienting the alignment guide over the surgical sight in preparation for using the alignment guide in conjunction with the surgical instruments. As suggested in FIG. 5A, the instrument guide 37 is attached to targeting platform 26, which is part of the overall trajectory system 25. A robotic arm 27 extends from targeting platform 26 and is connected to instrument guide 37. Using robotic arm 27, targeting platform 26 can extend or retract a short distance (a few centimeters) instrument guide 37 and can also rotate instrument guide 37. Targeting platform 26 is secured to the OR table by a series of adjustable positioning arms similar to those supporting camera 11 as described above. The instrument guide tracking array 40 (sometimes referred to as the "first marker array") is secured to instrument guide 37 and thereby allows camera 11 to track the location and orientation of instrument guide 37. In the illustrated embodiment, targeting platform 26 may be the Micromate™ personal robotic assistant system available from iSYS Medizintechnik GmbH, of Kitzbühel, Austria (d/b/a Interventional Systems).

In order to properly position the instrument guide 37, it is necessary to align the instrument guide with the planned trajectory of the surgical instrument or implant component (for instance, a pedical screw). Since targeting platform 26 can only make comparatively small adjustments to instrument guide 37, it is necessary for surgical personnel to manually position targeting platform 26 such that instrument guide 37 is oriented comparatively close (within a few centimeters) of the planned trajectory. Thereafter, this approximate position of the targeting platform may be secured in place with the locking hinge and locking sleeves on the adjustable positioning arms supporting the targeting platform. FIG. 5A also illustrates a control unit 35 which may be used to wirelessly control various functions of targeting platform 26 described herein.

Figure 6A:
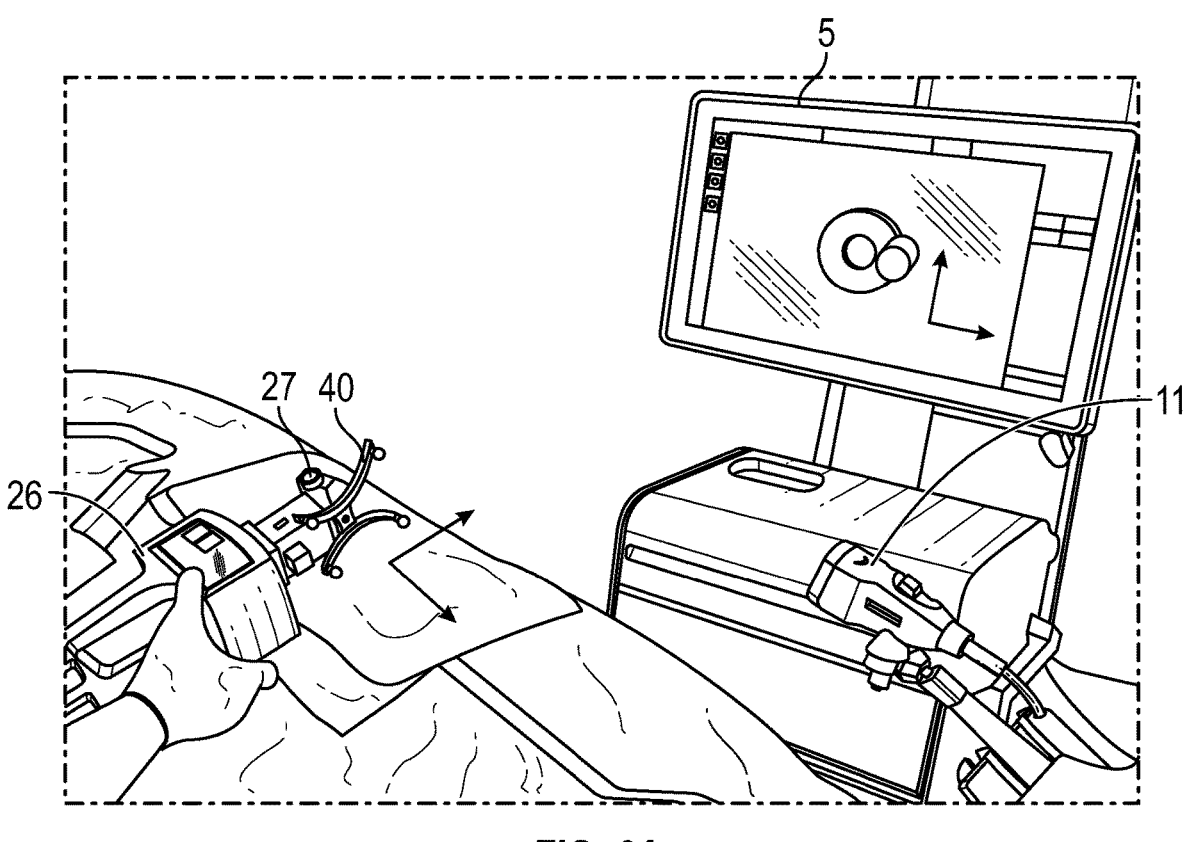
FIG. 6A illustrates one alignment user interface method of the surgical navigation system.
Figure 6B:
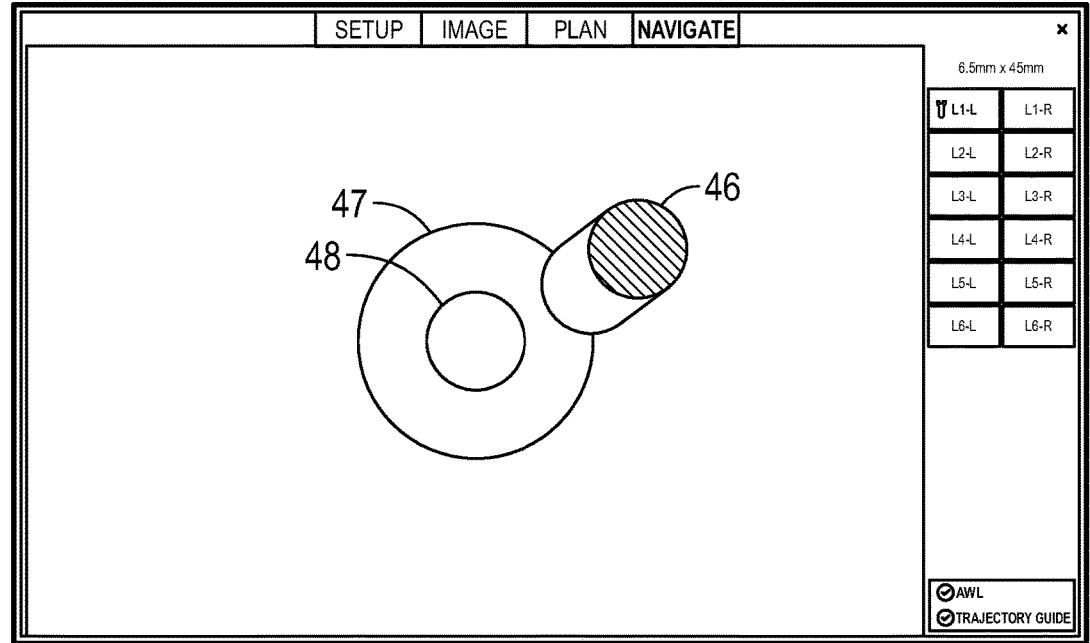
FIG. 6B illustrates the alignment user interface method with the instrument unaligned.
Figure 6C:
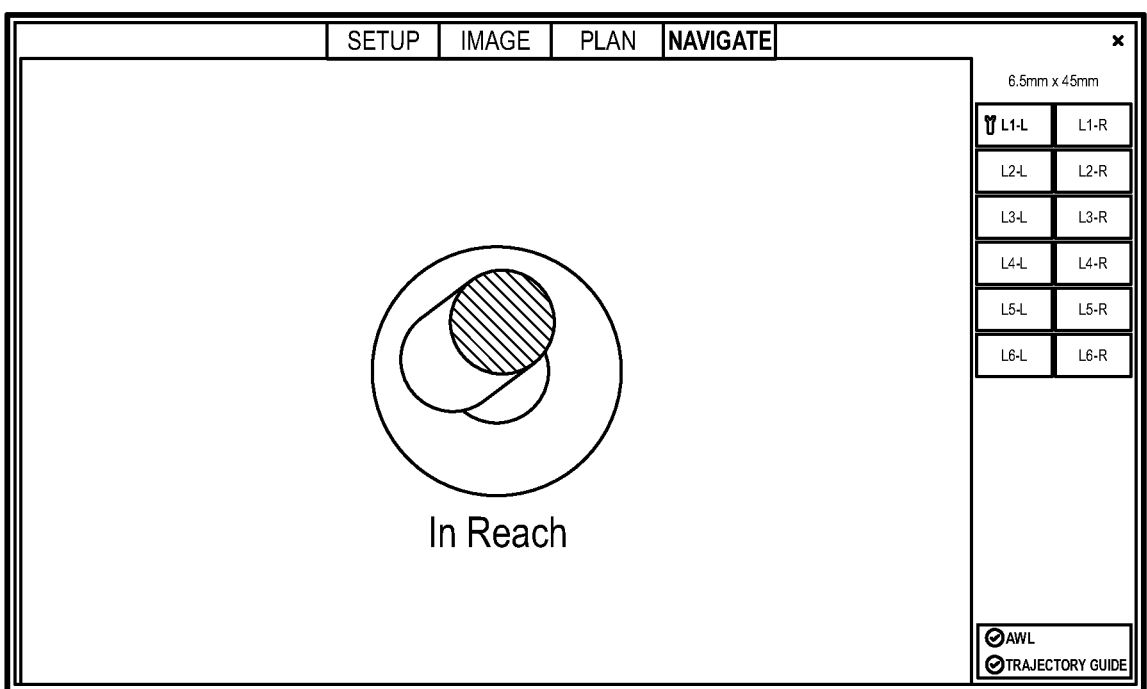
FIG. 6C illustrates the alignment user interface method with the instrument in reach.
Figure 19:
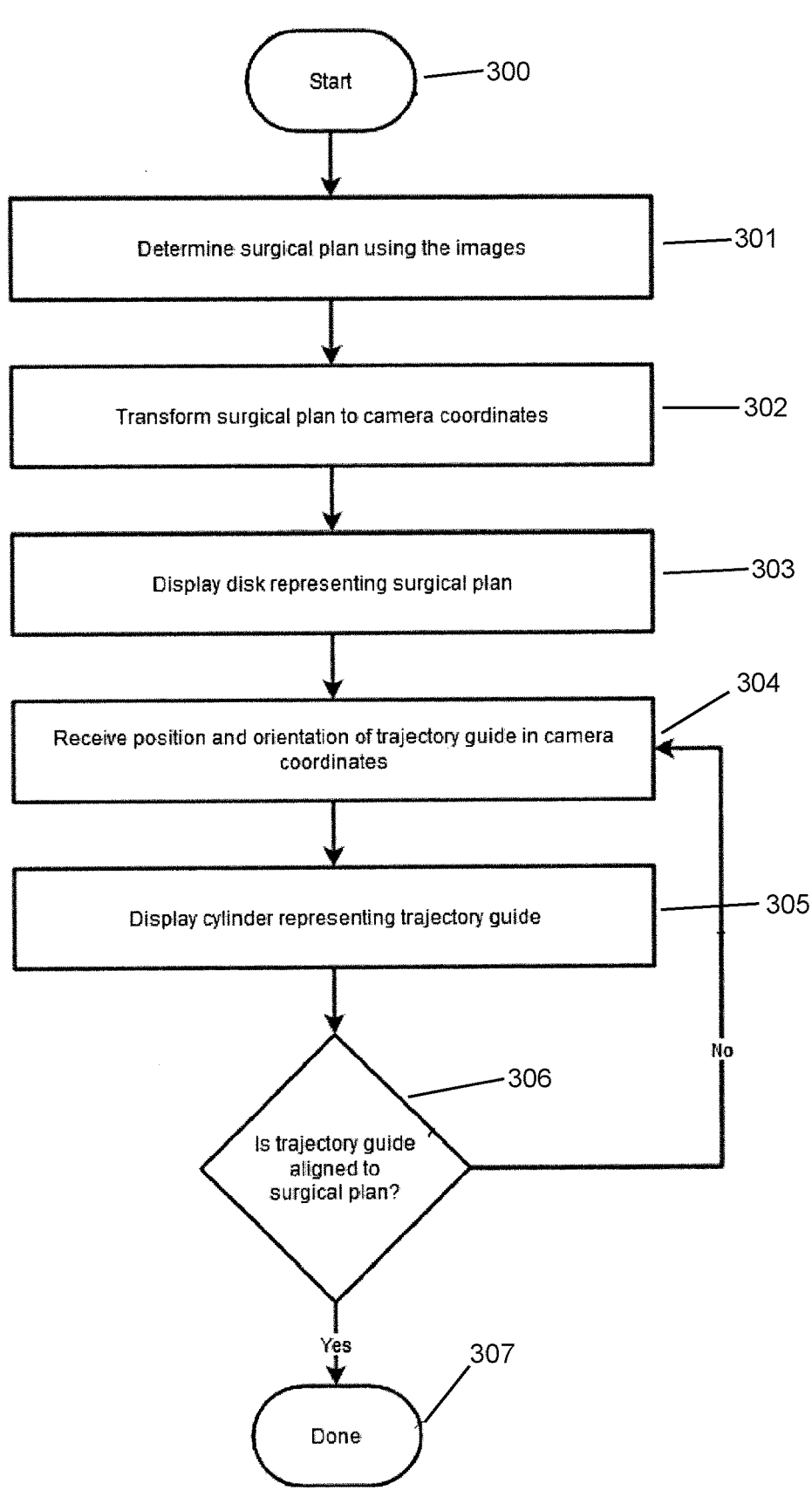
FIG. 19 illustrates a flowchart of steps in determining instrument guide alignment.

FIGS. 6A to 6D illustrate a novel user interface to assist surgical personnel in achieving this initial approximate positioning of targeting platform 26 and instrument guide 37. As suggested in FIG. 6A, the instrument guide tracking array 40 is positioned within view of camera 11. A general algorithm controlling this user interface is suggested in FIG. 19. Step 301 of FIG. 19 contemplates the input of a surgical plan by software which allows surgical personnel to overlay the trajectory of implant components on the radiological images. In step 302, the computer system transforms the image coordinates of the planned trajectories into camera coordinates. This allows the computer system in step 303 to display a disk or "trajectory target" representing each trajectory of the surgical plan. FIG. 6B illustrates the display of this trajectory target 47 representing the location and orientation of one of the planned implant trajectories (e.g., the initial implant component in the surgical plan). Similarly, shown on the display will be a 3-dimensional artifact 46 representing the instrument guide location and orientation as detected by the camera. In the illustrated embodiment, the trajectory target 47 is illustrated as annulus shaped and thus has an annulus inner diameter 48. The 3-dimensional artifact 46 is cylindrical in shape (thus will also be referred to as "cylinder 46") with a diameter approximating the annulus inner diameter 48. The software will track movement of the instrument guide tracking array 40 in 3-dimensions via data from the camera 11. Responsive to the camera data, the software updates the cylinder 46 image on the display as the instrument guide moves in the camera's field of view. This is represented in step 304 of FIG. 19 where the system receives the position and orientation of the instrument guide and coverts this information into camera coordinates. The updated position of cylinder 46 is shown on the display in step 306. If cylinder 46 is not aligned with trajectory target 47, the system receives the next position of the instrument guide.

As suggested in FIG. 6A, the instrument guide is positioned between a user and the display. The software displays and updates the position of cylinder 46 such that movement of the instrument guide 37 results in the same user's perspective of movement of cylinder 46 on the display. For example, leftward movement of the instrument guide from the user's perspective is shown on the display as leftward movement of cylinder 46. Similarly, movement of the instrument guide toward the user is shown on the display as downward movement of cylinder 46 on the display. Likewise, rotation of instrument guide 37 will be represented as the same direction of rotation of cylinder 46 on the display.

Figure 6D:
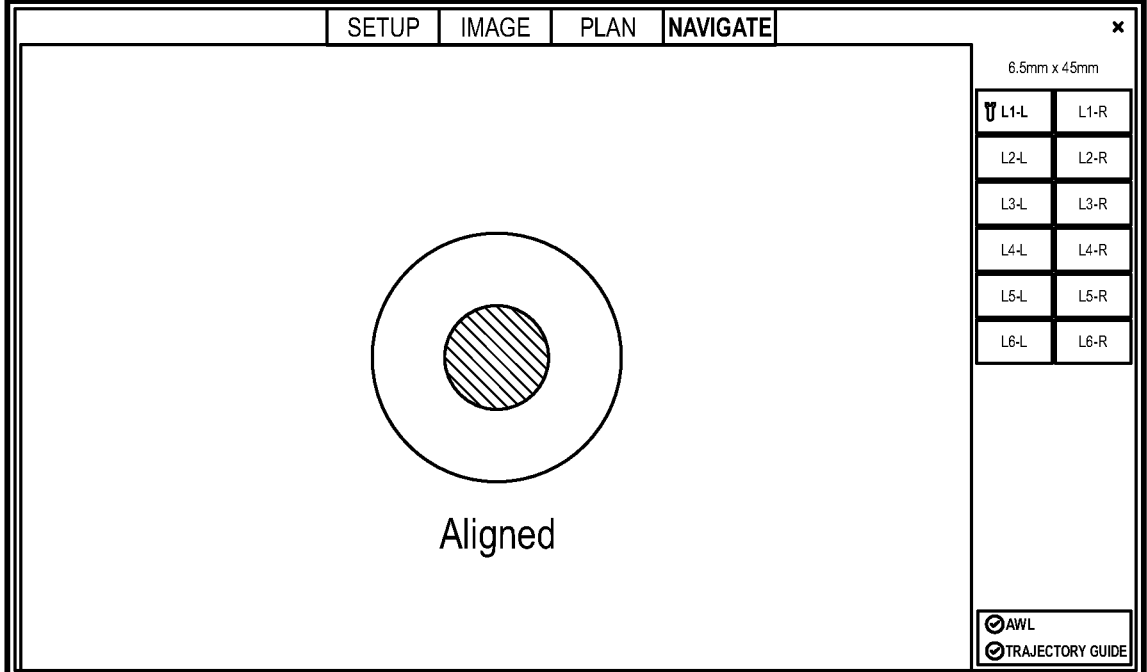
FIG. 6D illustrates the alignment user interface method with the instrument aligned.

As mentioned above, the robotic arm of targeting platform 26 has a limited range of mechanical "reach," i.e., the distance over which the targeting platform itself can control the positioning of the instrument guide. As suggested in FIG. 6C, when the system detects the instrument guide's distance from the planned trajectory is within the targeting platform's mechanical reach, the software will show an indicator on the display that this is the case (e.g., the "In Reach" indicator seen in FIG. 6C). After the instrument guide and robotic arm are moved by the user within the mechanical reach of the targeting platform, the computer may assume control and provide the targeting platform and robotic arm with instructions allowing the robotic arm to automatically align the instrument guide with the planned implant trajectory. This may be accomplished following basically the same steps 305 to 306 in FIG. 19. Upon alignment of the instrument guide with the planned trajectory, the condition in step 306 of FIG. 19 will be positive. In FIG. 6D, the cylinder 46 is shown centered within trajectory target 47 and an indicator such as "Aligned" is displayed.

Figure 7:
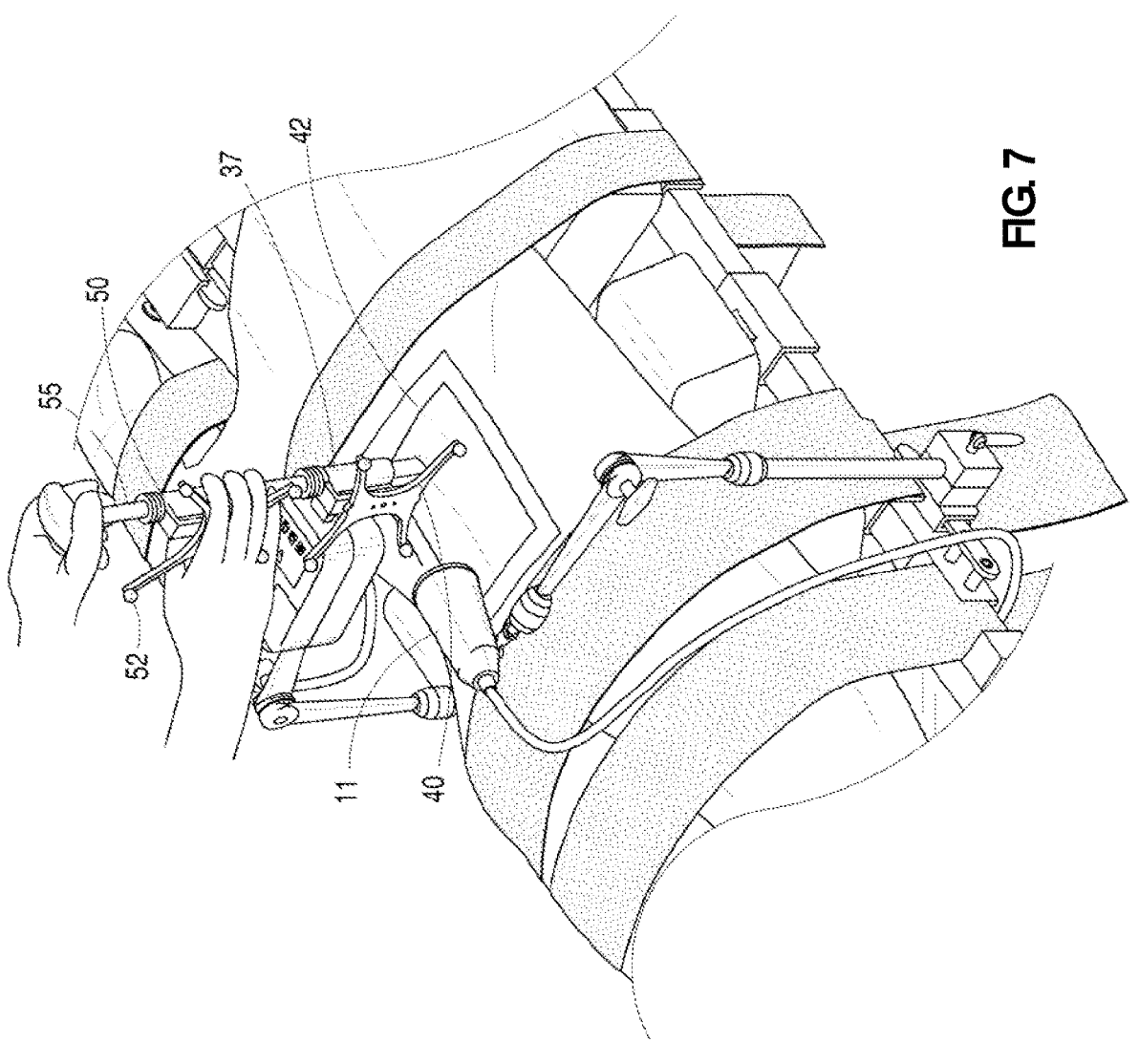
FIG. 7 illustrates a surgical instrument being utilized in conjunction with the instrument guide.
Figure 9A:
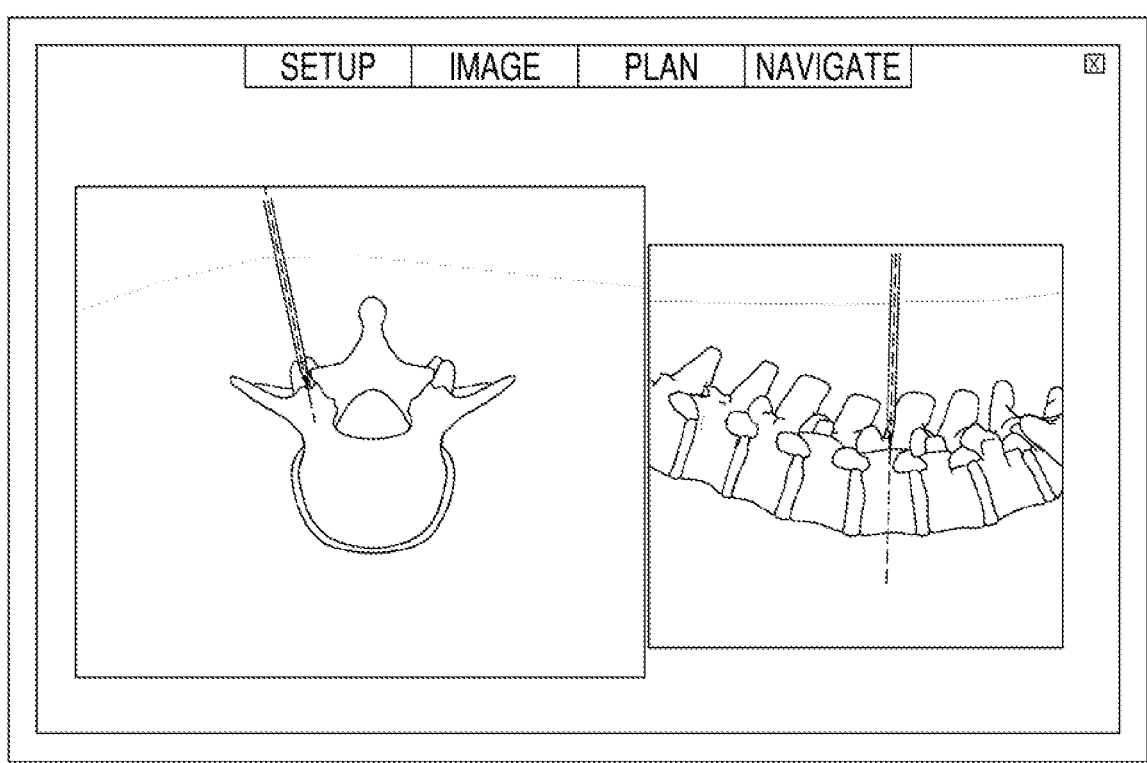
FIG. 9A illustrates a proper alignment image generated by the surgical navigation system.
Figure 9B:
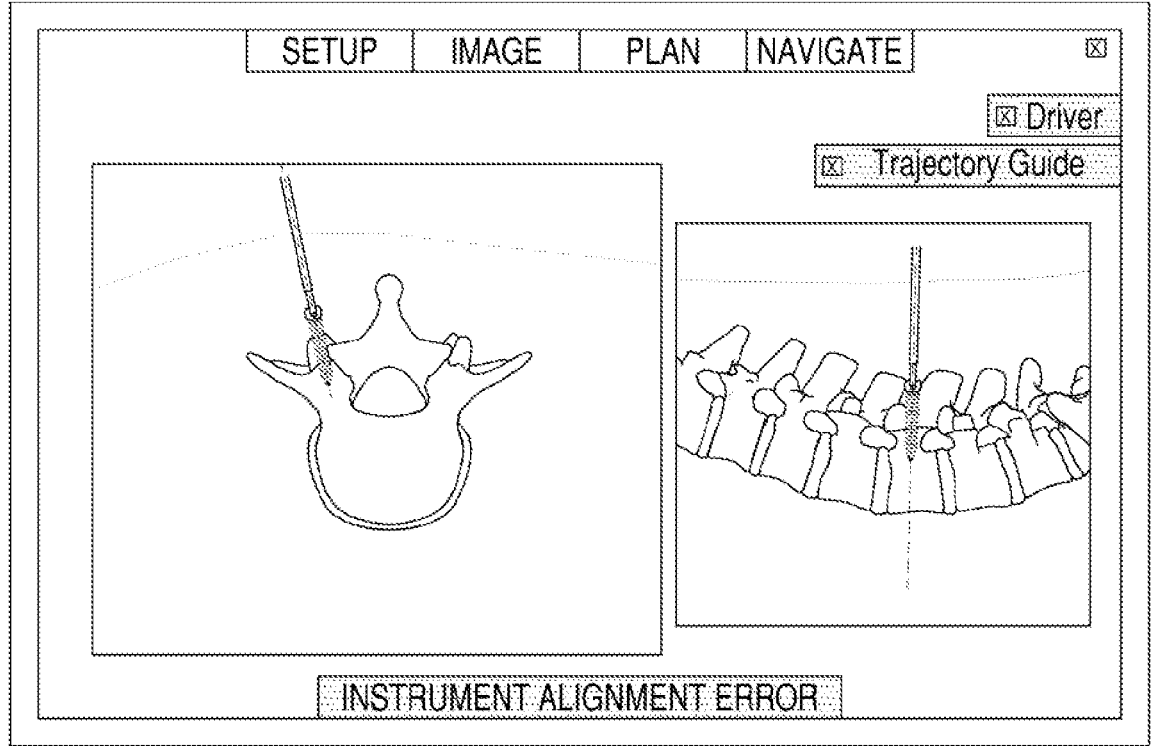
FIG. 9B illustrates an alignment error image generated by the surgical navigation system.

Another embodiment of the present invention is a system and method for generating more accurate trajectory estimates of surgical instruments during the surgical procedure. FIG. 7 illustrates the instrument guide 37 and its tracking array 40 aligned over the surgical site. Also illustrated is a user inserting a surgical instrument 55 (e.g., an awl) through the instrument guide 37. Fixed to the surgical instrument 55 is a surgical instrument tracking array 50 (also sometimes referred to as the "second tracking array" or "second marker array"). It will be understood that based on camera 11's detection of the medical instrument's tracking array, the navigation system software can determine the orientation of the tracking array (and therefore that of the medical instrument) and then show on the system display an estimated trajectory of the medical instrument superimposed on the radiological image of the patient anatomy at the surgical site (e.g., see FIGS. 9A and 9B).

Figure 8:
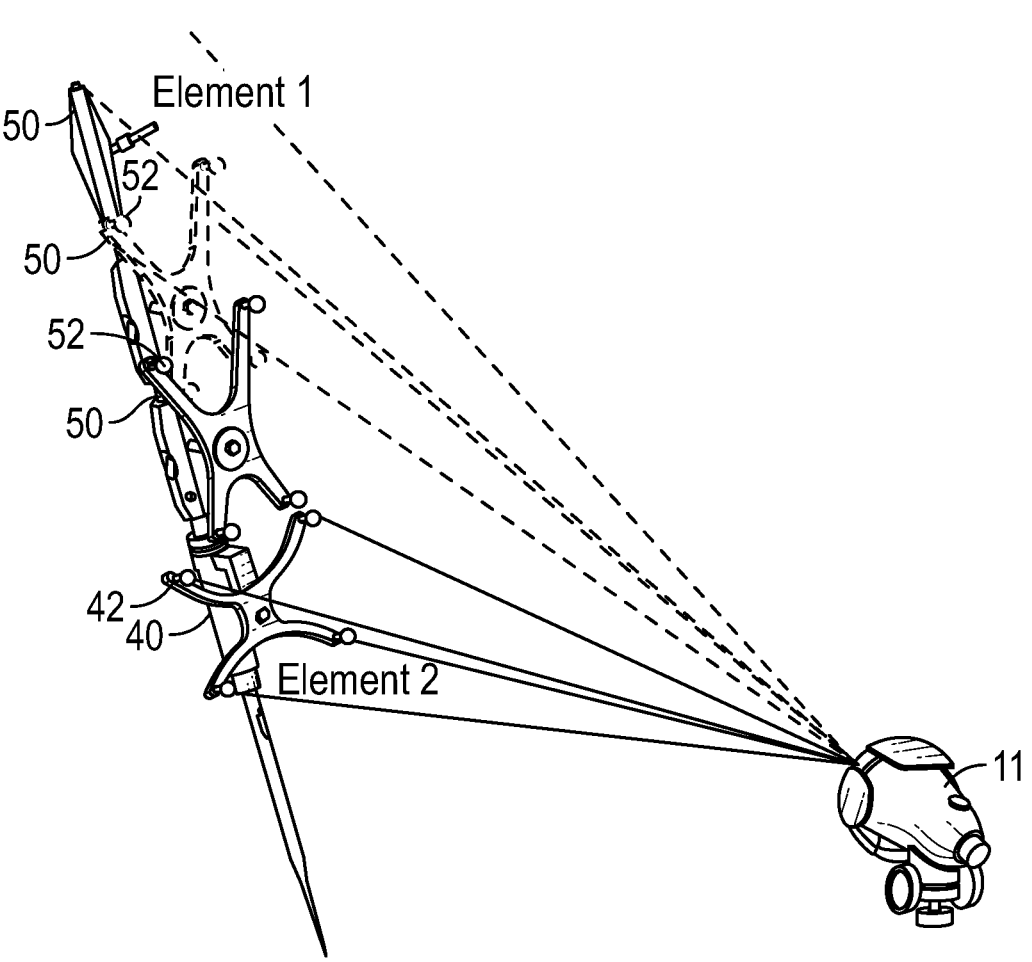
FIG. 8 illustrates conceptually a method of determining alignment using multiple marker arrays.

While calculating an instrument trajectory based upon the IR marker elements 52 of the instrument tracking array 50 may be acceptable for some applications, it is often desirable to have the most accurate instrument trajectory feasible. FIG. 8 illustrates a novel approach of estimating an instrument trajectory which utilizes the IR marker elements 52 of the instrument tracking array 50 in combination with the IR marker elements 42 of the instrument guide tracking array 40. In the FIG. 8 example, the camera would be detecting eight IR marker elements and in essence, treating the two tracking arrays at the time of image capture as an instantaneous, single rigid body, eight marker element array. Even as instrument tracking array 50 is changing position relative to the guide tracking array 40 (e.g., as the front tip of the surgical instrument is moving through the instrument guide and into the patient's body), the system software is calculating updated trajectories based upon the changing "eight marker element array" being detected by camera 11. In other words, the system is calculating in a first time frame a trajectory based upon the position of the IR marker elements of both the instrument tracking array 50 and guide tacker array 40; and then calculating in a second time frame an updated trajectory based upon a subsequent position of the IR marker elements of instrument tracking array 50 and guide tacker array 40.

It will be understood that not only the greater number of IR marker arrays, but also the greater geometrical spacing of the IR marker elements, lends itself to providing more accurate trajectory estimates. There could be many variations on this technique. As one example, it can be seen in FIG. 8 that the IR marker elements 52 of instrument tracking array 50 have a different spatial arrangement from the IR marker elements 42 of guide tracking array 40. This allows the system to distinguish the two tracking arrays and potentially give greater weight in the trajectory calculation to the IR marker elements of one tracking array versus the other, if that is likely to produce a more accurate trajectory estimate given the particular circumstances of the instruments and/or surgical procedure.

Figure 10:
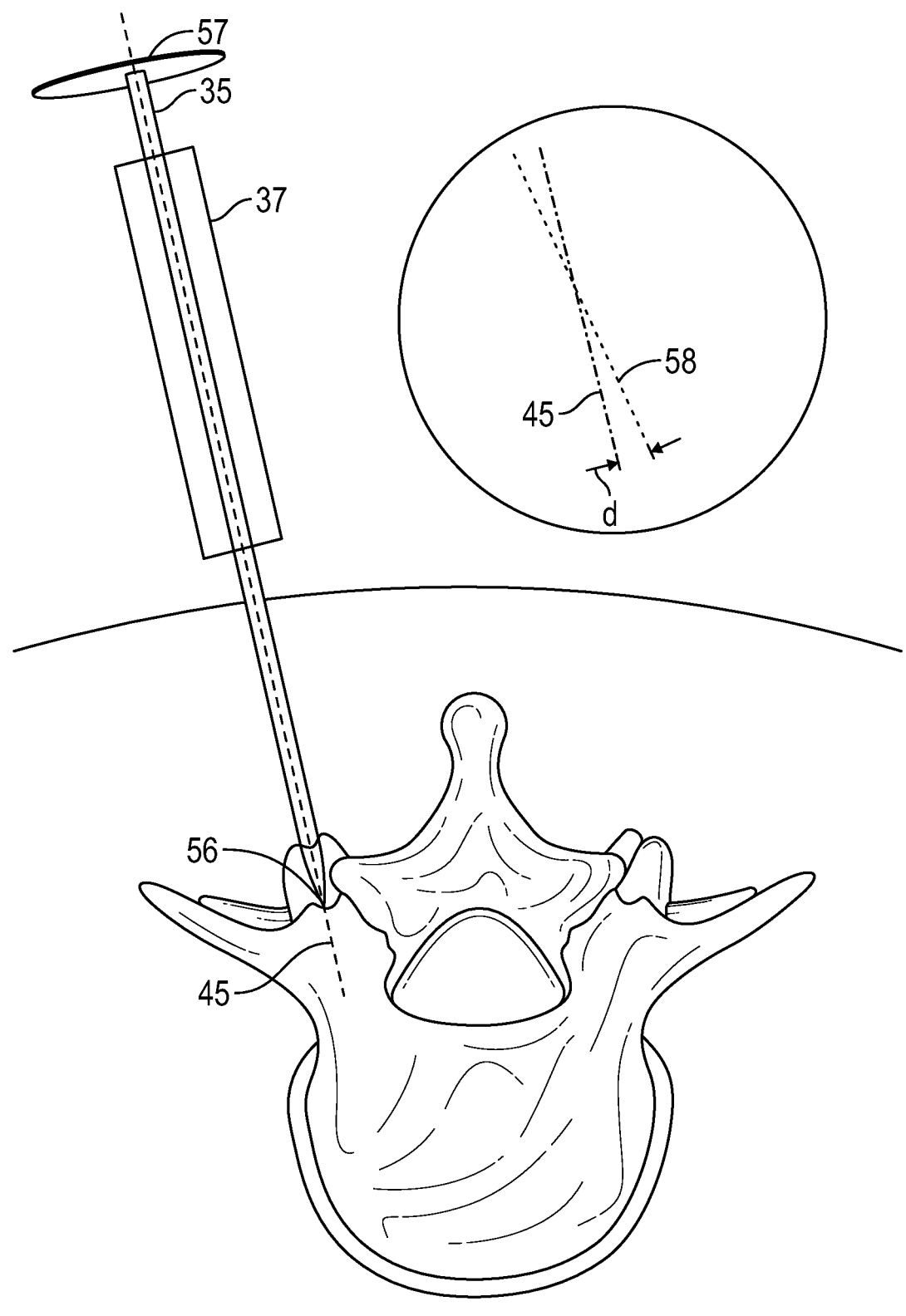
FIG. 10 illustrates conceptually the alignment of the surgical instrument and surgical guide at the surgical site.

A further aspect of the present invention is a system and method for indicating an acceptable degree of alignment of a surgical instrument. As suggested schematically in FIG. 10 detail, the system will identify the position of both the instrument tip 56 and the instrument hind 57. In one example, this may be done based on the instrument tracking array 50 alone. Because the system knows the dimensions of the instrument and how the tracking array 50 is fixed to the instrument, determining the position of the tracking array 50 allows the system to calculate the position of the instrument tip and hind. In another example, the lower end of the instrument guide 37 is determined (using a similar method based on the location of the guide tracking array 40) and the location of the lower end of the instrument guide is utilized in estimating the location of the instrument tip. As a still further alternative, the method described in FIG. 8 could be used in determining the tip and hind of the instrument.

Once the position of the instrument tip and hind are calculated, an estimated instrument trajectory 58 may be calculated based on the tip and hind positions. As suggested in FIG. 10, a comparison of the planned surgical trajectory 45 and the estimated instrument trajectory 58 can then be made. The offset distance "d" between the planned surgical trajectory 45 and the estimated instrument trajectory 58, for example at instrument tip 56, may be calculated to determine the instrument trajectory variation from the planned trajectory. Naturally, this offset distance "d" could be calculated at the hind, or conceivable anywhere else along the instrument. When the offset distance "d" is greater than a set threshold value, the system will present on the display a warning of misalignment (see for example FIG. 9B). Similarly, the warning of misalignment could include presenting on the display the image of the surgical instrument in red. Likewise, the image of the surgical instrument could be presented on the display in green if the offset distance is less than the threshold. In certain example embodiments, this threshold is no greater than approximately 2 mm.

Figure 21:
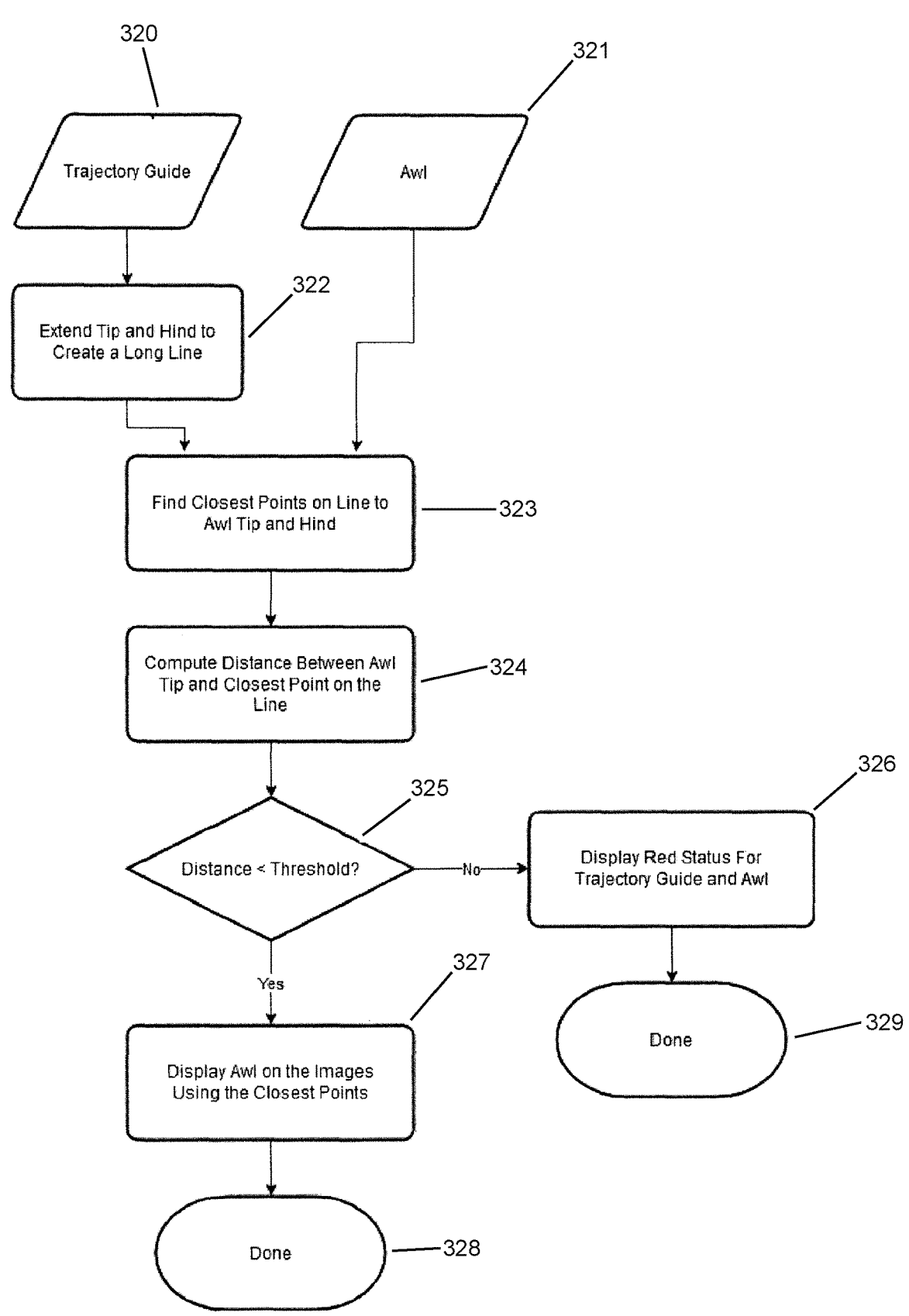
FIG. 21 illustrates a flowchart of steps in determining instrument trajectory alignment.

FIG. 21 is a flowchart of one method for determining and indicating acceptable alignment of a medical instrument with a planned surgical trajectory. In steps 320 and 321, the system determines the location of the tip and hind of the instrument guide and the surgical instrument (e.g., an awl) based on their respective tracker arrays and the known dimensional relationship between the instrument guide and surgical instrument and their respective tracker arrays. In step 322, the tip and hind of the instrument guide are used as two points to generate an extended line. Since the instrument guide will have been oriented to follow the planned surgical trajectory, this extended line is also along the planned surgical trajectory. In step 323, the system finds the closest points on this line to the surgical instrument's tip (and/or hind). Step 324 computes the distance between the awl tip and the closest point on the line. If this distance is less than a given threshold in step 325, then the system displays in step 327 the surgical instrument on the radiological images using the closest points of the tip to the line. If the distance is greater than the threshold, then step 326 displays a red status for the awl and the instrument guide.

Figure 11:
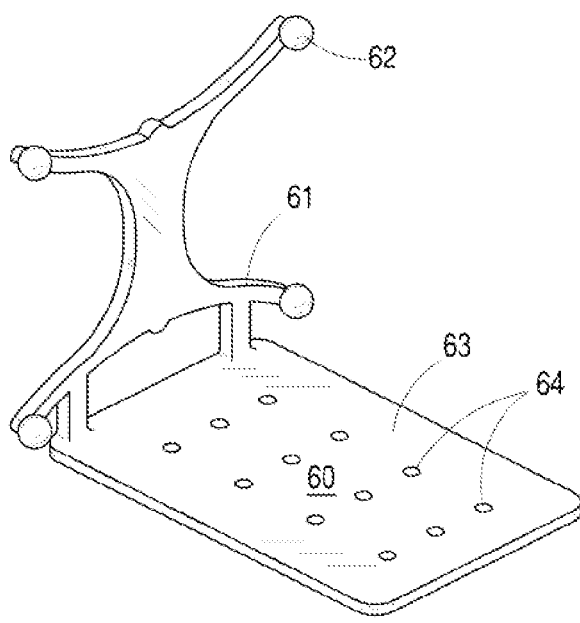
FIG. 11 illustrates one marker array of the present invention.

As suggested previously in reference to FIG. 4, certain embodiments of the present invention involve the use of a registration array 60 when generating radiological images. FIG. 11 illustrates one embodiment of registration array 60 in more detail. This example of registration array 60 is formed of the marker frame (or marker support structure) 61 extending off of plate section 63. The marker frame 61 supports the IR marker elements 62 and a series of apertures in plate section 63 will form the "fiducials" 64, which are explained in more detail below.

Figure 14:
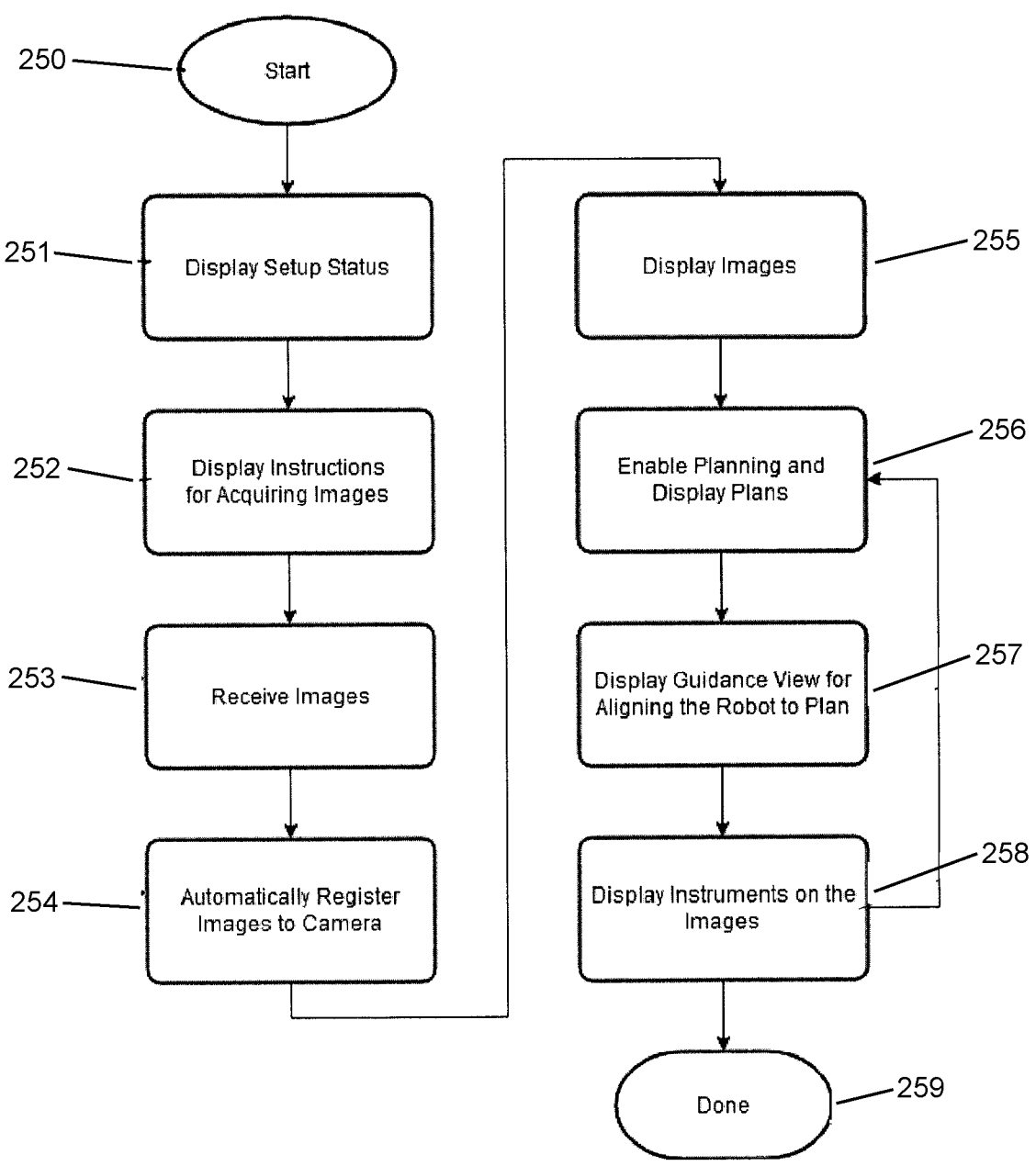
FIG. 14 illustrates a flowchart of acquiring and registering initial navigation images.

FIG. 14 provides a general overview of software functions performed by one embodiment of the invention. At start 250, the system will display a setup status in step 251. Typically, the next step (252) will be displaying instructions for acquiring radiological images. The system will receive the radiological images at step 253 and automatically register the images to the camera in step 254. Certain aspects of the registration process are discussed in greater detail elsewhere herein. After the images have been acquired and registered, they will be displayed in step 255. Step 256 will allow surgical personnel to enable surgical planning and to display such plans. For example, the position of pedicle screws in the patient's anatomy can be determined and displayed on the radiological images as part of the planning process. Step 257 will display a guidance view (one example of which is described above) to assist in aligning an instrument guide in the proper trajectory over the surgical site. Step 258 will display instruments in relation to the radiological image as the instruments are brought into the camera's field of view (e.g., FIG. 9A).

Figure 20:
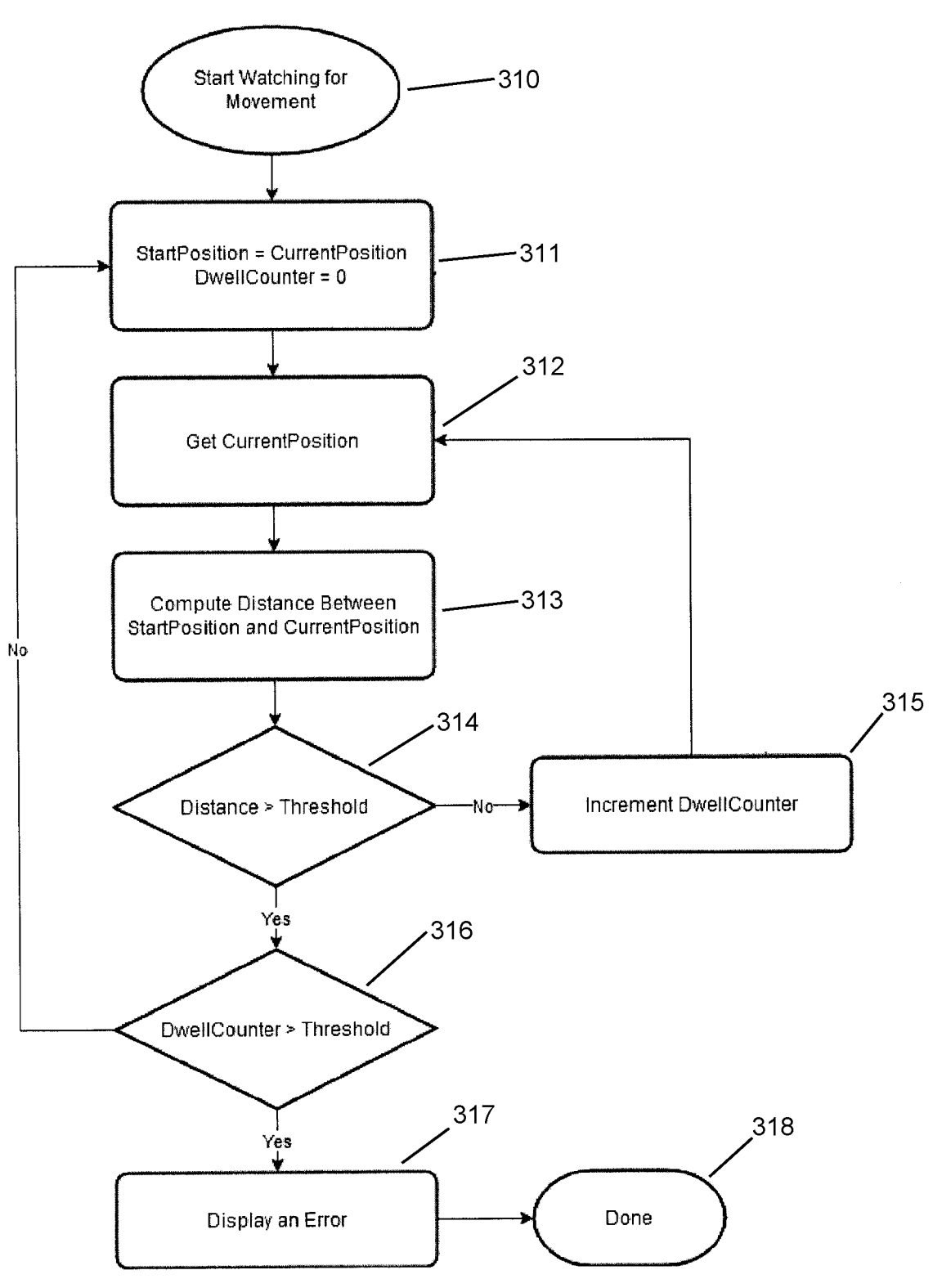
FIG. 20 illustrates a flowchart of steps in determining unexpected marker array movement.

Prior to generating the radiological images, registration array 60 is positioned on or adjacent to the surgical site. FIG. 4 shows the registration array 60 being secured to the patient at the surgical site with tape, but other fixing means could be employed as long as the registration array 60 is readily removable after the radiological imaging is complete. In most imaging/registration techniques, it is important that the registration array not move relative to the surgical site while the radiological images are being generated. Thus, another aspect of the present invention is a method for monitoring the registration array for movement during the imaging process. One example of this process is suggested in the flowchart of FIG. 20. In step 310, the computer system, through camera 11, begins monitoring registration array 60 (or more specifically, the IR marker elements 62 on registration array 60) for movement. In step 311, the Start Position is set equal to the Current Position as most recently detected by camera 11. A Dwell Counter is set to zero. In the loop of steps 312 to 315, the computer system continuously (e.g., at the frame speed of the system) determines the Current Position of the registration array and then determines the difference (in displacement or distance) between the Start Position and the then Current Position. As used herein, "frame speed" means the rate at which the system can calculate the position of the tracker arrays and update the position of their respective instruments on the display. As long as the difference in distance in step 314 is not greater than a distance threshold, the dwell counter is incremented in step 315 and the loop continues. This distance threshold could vary, but in one example the distance threshold is 1 mm.

If the distance is greater than the distance threshold, then step 316 determines if the Dwell Counter is greater than a counter threshold in step 316. If this condition is not met, then the Start Position is reset to the then Current Position. If this condition is met, then the system displays an array movement error indicator in step 317. The counter threshold represents a given amount of time (expressed in terms of the number of loops where the Dwell Counter is incremented) during which the distance threshold is not exceeded. In essence, the time during which the registration array does not move an appreciable degree, i.e., a degree to which unacceptable error would be introduced into the registration process. Naturally, rather than counting software loops, the counter threshold could simply be a stated amount of time and the Dwell Counter could be time which has elapsed. In effect, the FIG. 20 algorithm will not trigger an error or alarm if there are a series of closely spaced changes of the registration array's position, for example, the registration array constantly moving in the camera's field of view while OR personnel are fixing the registration array over the surgical site. However, if the registration array moves after a period of remaining stationary, it is more likely the movement was unintentional (e.g., during the radiological imaging process) and will generate an error notice. In one embodiment, the threshold time in step 316 is set at three seconds, but in other embodiments, it could be as little as 1 second.

Figure 12:
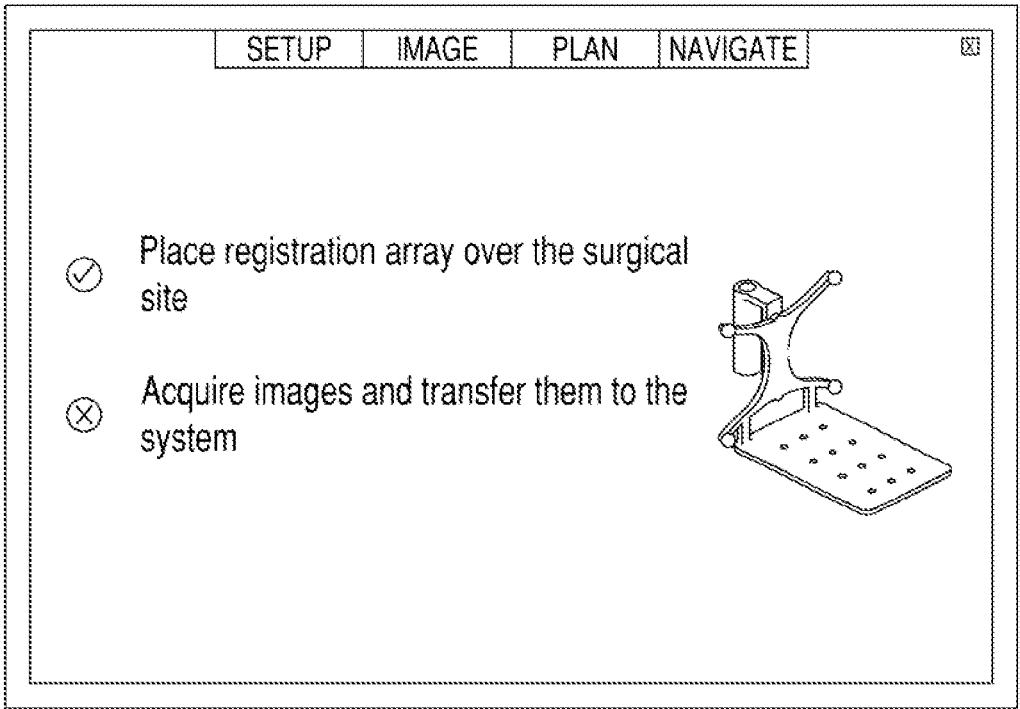
FIG. 12 illustrates a system user interface indicating marker array location error.

FIG. 12 suggests one example error message that could be generated if the system detects movement of the registration array during the generation of the radiological images. Similar error messages could be generated if the camera could not detect the array in its field of view or the system could not detect the plate of the registration array within radiological images.

A still further aspect of the present invention relates to the structure of the registration array 60 seen in FIG. 11. It can be seen that the plate section 63 is generally rectangular and will have a series of "fiducials" 64 formed on the plate section. In FIG. 11, the fiducials are apertures or sharp depressions formed in the plate, but the fiducials could also be raised section, i.e., mounds, or small spheres adhered to the plate section. While FIG. 11 shows twelve fiducials, there could be fewer or more fiducials 64 with many embodiments having at least six fiducials. The marker support structure 61 extends upwardly at or near (e.g., within 20% of the plate's overall length) one of the shorter edges of rectangular plate section 63. The marker support structure 63 is in a plane generally perpendicular (e.g., within +/−30° from perpendicular) to the plane containing plate section 63. Preferred embodiments of the marker support structure will include at least four spherical IR marker elements 62.

Figure 13A:
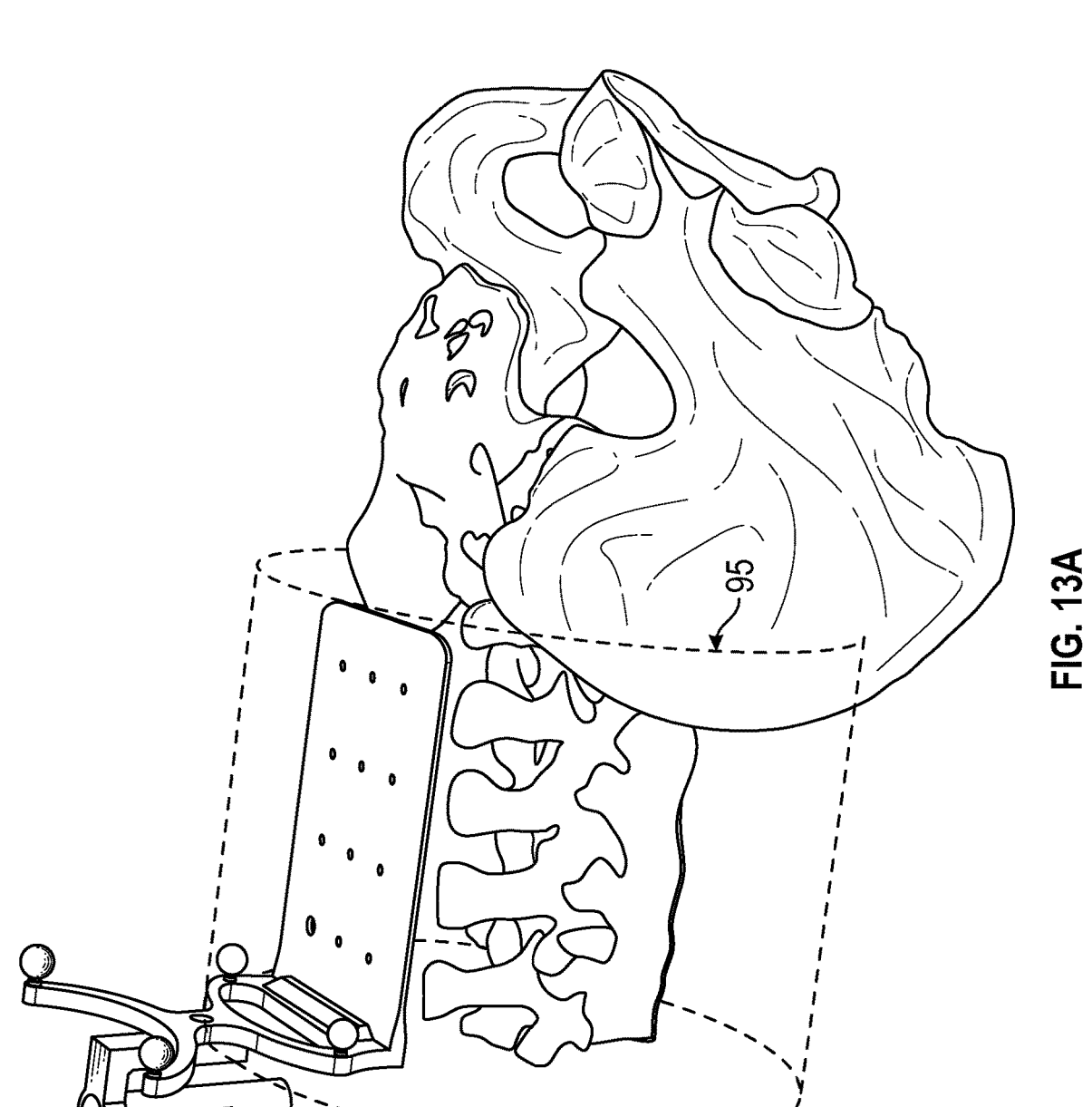
FIG. 13A illustrates conceptually the marker array in the radiological image volume.

FIG. 13A suggests the registration array 60 used in conjunction with the capture of a 3D radiological image having an image volume 95. In this embodiment, the length of plate section 63 should generally conform to the length of image volume 95, with the length of plate section 63 being at least 75% a length of the image volume. In many embodiments, plate section 63 will have a length of between 150 mm and 300 mm and a width of between 50 mm and 150 mm.

Figure 15:
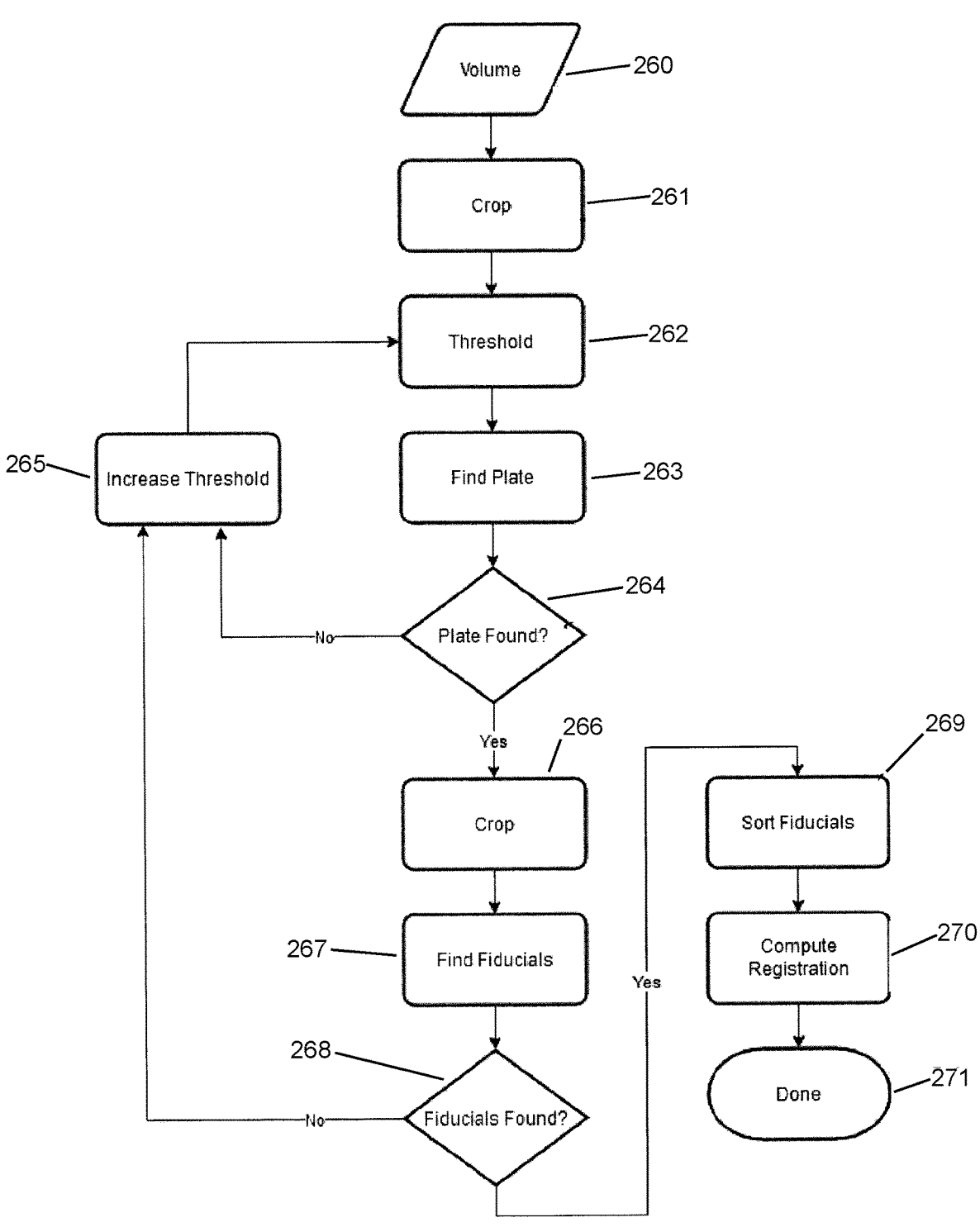
FIG. 15 illustrates a flowchart of an auto-registration algorithm.

When the image volume 95 of the radiological image includes the plate section 63 as seen in FIG. 13A, the fiducials 64 may be used to assist in registering the radiological image to the 3D space viewed by camera 11. However, prior to registering the image, the fiducials must be identified within the 3D image data by software running on the computer system. As suggested in the flowchart of FIG. 15, the image volume is received in step 260 and then in step 261, the volume is cropped to include the posterior portion (e.g., half) of the volume where the registration plate is expected to be found. Cropping this volume (sometimes referred to as the "first" image volume) reduces the amount of data processed when searching for the plate and therefore reduces processing time. In step 262, an initial threshold is set for an image feature which is likely to distinguish image elements related to the plate section 63 as opposed to other image elements (e.g., the bone structure seen in FIG. 13A). In one embodiment, the image feature constituting the threshold is a greyscale, i.e., image elements related to the plate are likely to be a different greyscale value than other image elements. Steps 263 and 264 determine whether the plate can be identified out of the rest of the cropped image volume. If not, the threshold is increased (e.g., greyscale value increased) and another attempt is made to find the plate. Therefore, the process for finding the registration plate includes the step of iteratively increasing an image threshold.

Figure 16:
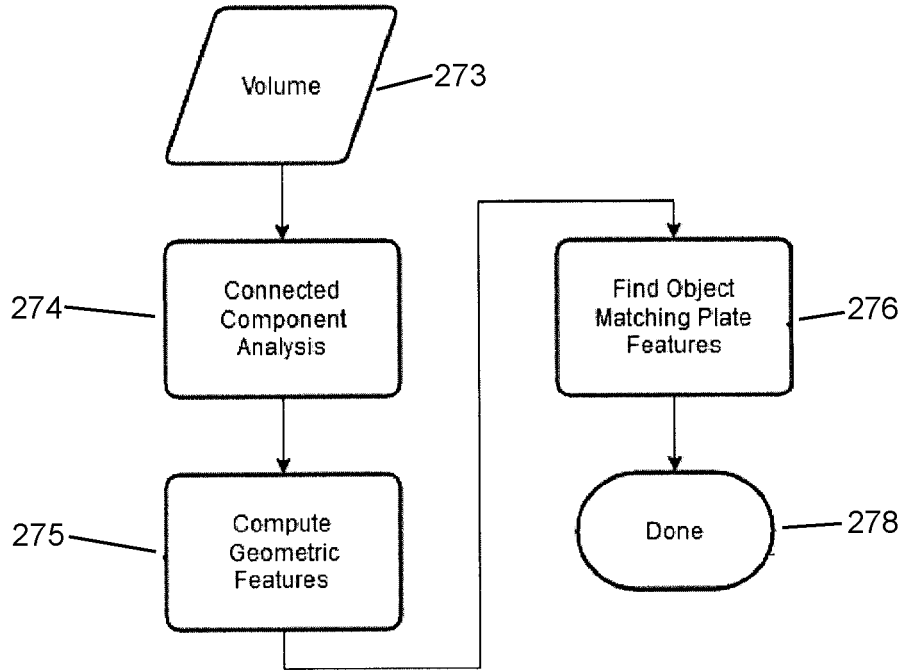
FIG. 16 illustrates a flowchart of an algorithm to locate the registration plate.

One example algorithm for finding the plate in step 263 is shown in FIG. 16. Step 273 of FIG. 16 begins with the first cropped volume and in step 274 performs a connected component analysis to identify all objects within the volume. Then in step 275, the geometric features of each object, including size, shape, and volume are determined. Finally in step 276, the object best matching the geometric features of the plate is chosen as the result.

Figure 13B:
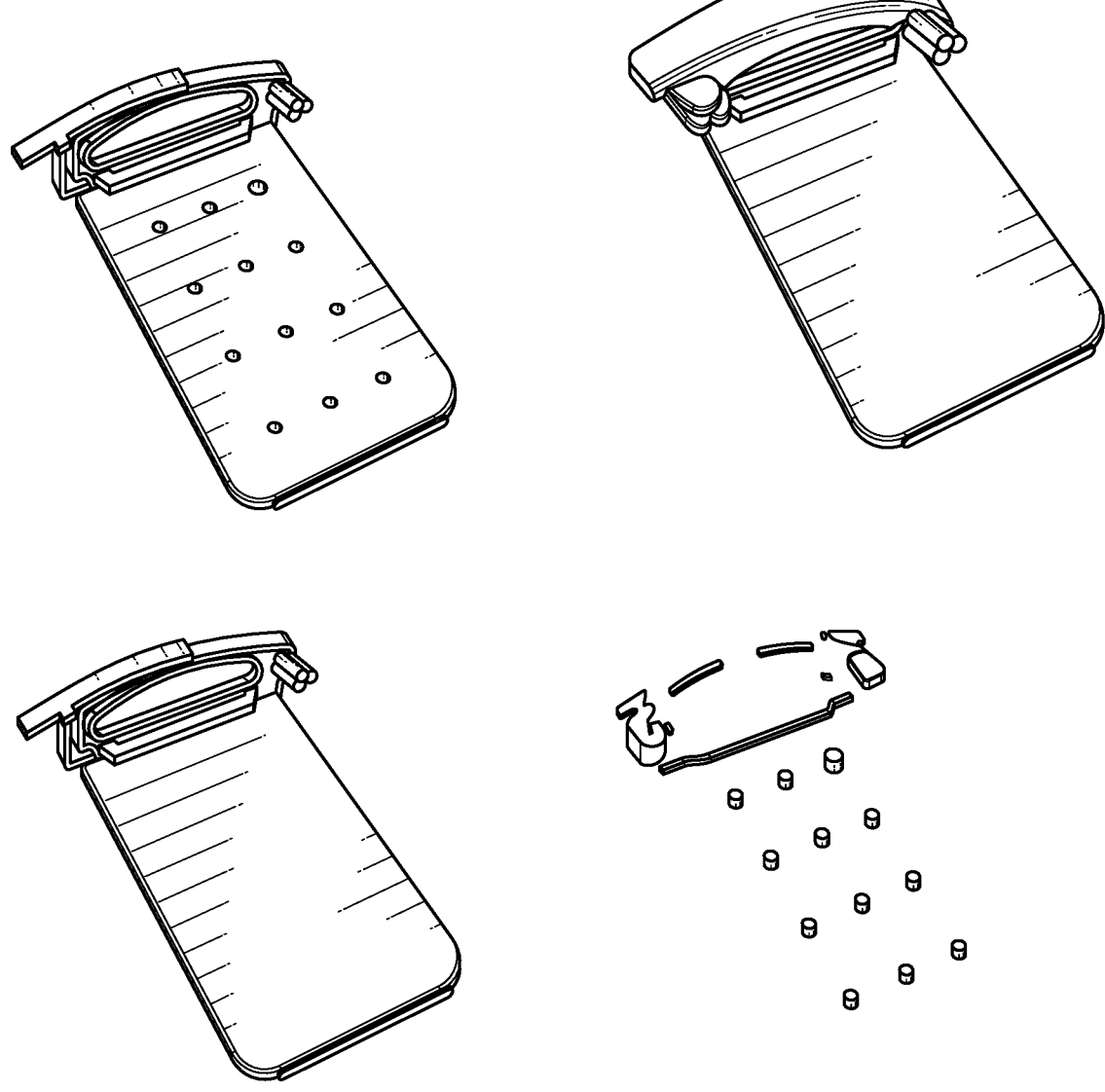
FIG. 13B illustrates conceptually a software method for identifying marker array elements.
Figure 17:
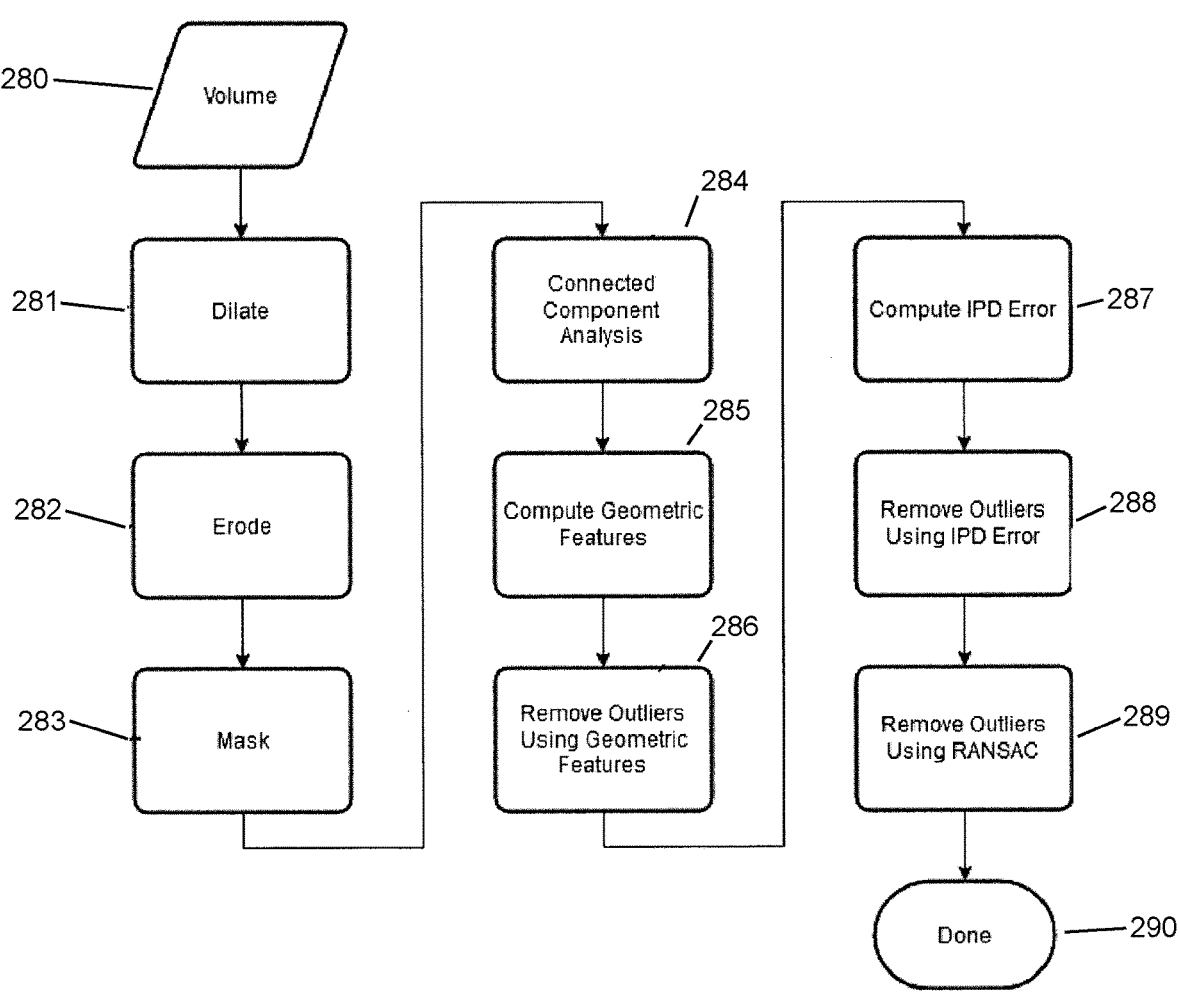
FIG. 17 illustrates a flowchart of an algorithm to identify registration plate fiducials.

Returning to FIG. 15 and step 264, if the plate is found, step 266 crops a "second" image volume associated with the identified plate (e.g., about 120% of the plate volume) in preparation for searching for the fiducials in the plate. In step 267, the program begins searching for the fiducials using, in one example, the algorithm seen in FIG. 17. The second image volume in step 280 is subject to the initial processing steps of dilation, erosion, and masking in steps 281, 282, and 283. As suggested in FIG. 13B, the initial version of the second image volume (showing the fiducial apertures) is dilated in order to generate an image showing the fiducials apertures largely filled. Next, erosion further eliminates any visual vestiges of the fiducial apertures. Then, the initial image is used as a mask of the eroded image to create a final representation constituting a mirror of the fiducial apertures, i.e., a series of small cylinders in place of the fiducial apertures. Next in FIG. 17, step 284 utilizes connected component analysis to find all objects (e.g., the cylinders now representing the fiducials) within this latest image of the fiducials. Step 285 computes the geometric shape of all objects found in step 284, while step 286 uses geometric features such as elongation and volume to eliminate objects (remove outliers) which do not match the expected cylindrical size and shape of the fiducials. In step 287, inter-point distances (IDPs) are computed for the remaining objects and the locations of these objects are compared to the known grid spacing of the fiducials in the original plate in order to compute the IDP error related to each object. In step 288, any objects not corresponding to the grid spacing (i.e., having an unacceptable IDP error) are removed as outliers.

Finally, in step 289, a random sample consensus (RANSAC) analysis is utilized to identify and remove any objects not in the same plane as the majority of fiducials (i.e., the presumptive plane of the plate).

Figure 18:
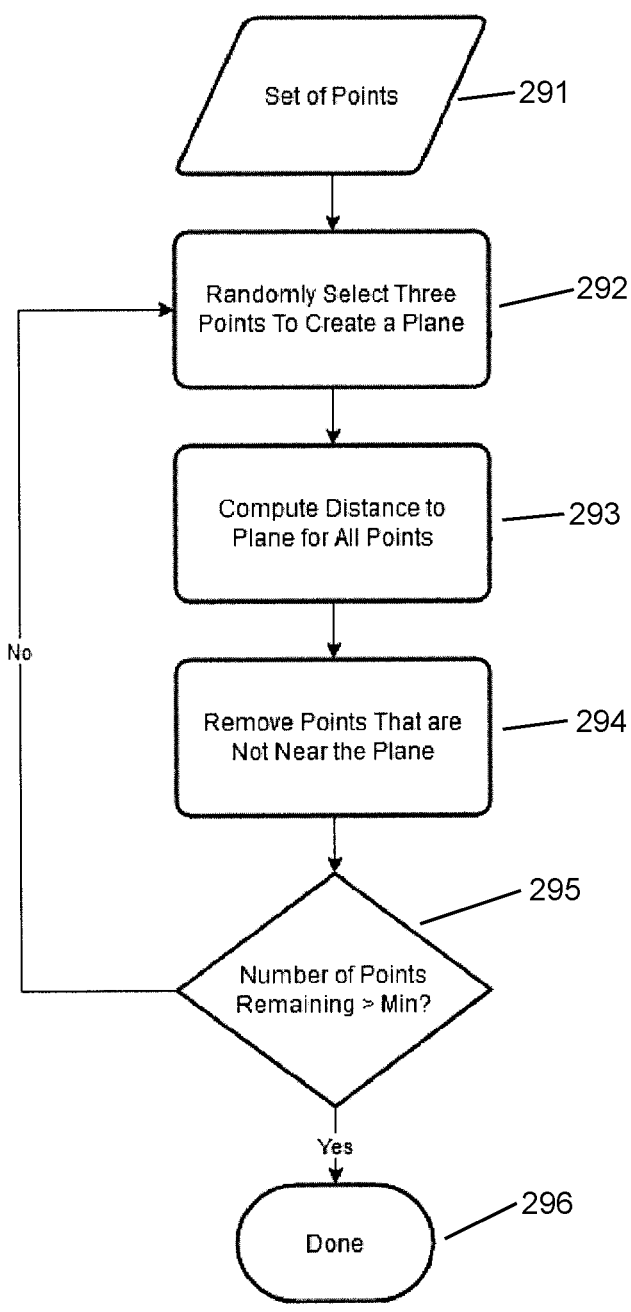
FIG. 18 illustrates a flowchart of an algorithm to remove points not in the plane of the plate.

FIG. 18 suggests one example of the RANSAC analysis. A set of points representing the objects existing after the IDP error analysis is established in step 291. In step 292, three points are randomly selected to define a plane and then step 293 computes a distance to the plane for all points. Step 294 removes points that are not on or near the plane. If the number of points remaining are not greater than a given minimum in step 295 (i.e., the expected number of fiducials), then the process is restarted and a new plane defined. If the number of remaining points is greater than the minimum, then it is assumed the remaining points correspond to the fiducials in step 296. Returning to FIG. 15, the position of the fiducials are sorted in step 269 to correspond to the fiducial model in marker array coordinates (i.e., coordinates determined by the camera viewing the marker elements extending above the registration plate). In other words, because the system knows the position relationship between the fiducials and the IR marker elements on the registration array 60, the position of the fiducials in the camera's coordinate system can be generated. Finally, in FIG. 15 step 270, a fiducial registration is computed that transforms points from camera coordinates to image coordinates.

The term "about" will typically mean a numerical value which is approximate and whose small variation would not significantly affect the practice of the disclosed embodiments. Where a numerical limitation is used, unless indicated otherwise by the context, "about" means the numerical value can vary by +/−5%, +/−10%, or in certain embodiments +/−15%, or even possibly as much as +/−20%. Similarly, "substantially" will typically mean at least 85% to 99% of the characteristic modified by the term. For example, "substantially all" will mean at least 85%, at least 90%, or at least 95%, etc.

While preferred embodiments of the present disclosure have been described, it is to be understood that the embodiments described are illustrative only and that the scope of the invention is to be defined solely by the appended claims when accorded a full range of equivalents, with many variations and modifications naturally occurring to those skilled in the art from a perusal hereof.

What is claimed is:

1. A surgical navigation method for indicating an alignment of a surgical instrument, the method comprising the steps of:

(a) providing a surgical navigation system including (i) a computer and display, (ii) data representing a 3D radiological image of a patient surgical site, (iii) an instrument guide having a first marker array, (iv) the surgical instrument having a second marker array, and (v) an optical sensor configured to detect markers on the first and second marker arrays;

(b) aligning the instrument guide by positioning the instrument guide in the general position of a pre-established trajectory line using the display, which displays (i) a two-dimensional disc representing the pre-established trajectory line and (ii) a three-dimensional cylinder representing the guide trajectory line, such that alignment between the pre-established trajectory line and the guide trajectory line is achieved when the three-dimensional cylinder is aligned with and fits within a central circle of the two-dimensional disc;

(c) identifying a tip and hind of both the instrument guide and the surgical instrument based upon detection of the marker arrays by the optical sensor;

(d) defining a guide trajectory line with the tip and hind of the instrument guide;

(e) calculating an offset distance between the guide trajectory line and at least one of the tip or hind of the surgical instrument;

(f) calculating whether the offset distance is greater than a threshold; and (g) presenting on the display a warning of misalignment if the offset distance is greater than the threshold.

2. The method of claim 1, wherein (i) an instrument orientation is determined based upon the tip and hind of the surgical instrument, and (ii) the warning of misalignment includes presenting on the display the guide trajectory line and an image of the surgical instrument, in the instrument orientation, super-imposed on the 3D radiological image.

3. The method of claim 2, wherein the warning of misalignment includes presenting on the display the image of the surgical instrument in red.

4. The method of claim 3, wherein the image of the surgical instrument is presented on the display in green if the offset distance is less than the threshold.

5. The method of claim 1, wherein the first marker array and the second marker array are registered to the 3D radiological image.

6. The method of claim 1, wherein at least a portion of the surgical instrument is inserted into the instrument guide when calculating the offset distance between the guide trajectory line and the tip or hind of the surgical instrument.

7. The method of claim 1, wherein a position of the optical sensor is fixed relative to the patient surgical site.

8. The method of claim 1, wherein the threshold is less than 2 mm.

9. The method of claim 1, wherein the offset distance is a distance between the surgical instrument tip and a closest point to the surgical instrument tip along the guide trajectory line.

* * * * *